US011214833B2

(12) United States Patent
Skog et al.

(10) Patent No.: US 11,214,833 B2
(45) Date of Patent: Jan. 4, 2022

(54) PROFILING MICROVESICLE NUCLEIC ACIDS AND USES THEREOF AS SIGNATURES IN DIAGNOSIS OF RENAL TRANSPLANT REJECTION

(71) Applicants: Exosome Diagnostics, Inc., Waltham, MA (US); The Brigham and Women's Hospital, Inc., Boston, MA (US)

(72) Inventors: Johan Karl Olov Skog, Charlestown, MA (US); Jamil Azzi, Boston, MA (US)

(73) Assignees: Exosome Diagnostics, Inc., Waltham, MA (US); The Brigham and Women's Hospital, Boston, MA (US)

( * ) Notice: Subject to any disclaimer, the term of this patent is extended or adjusted under 35 U.S.C. 154(b) by 373 days.

(21) Appl. No.: 16/098,500

(22) PCT Filed: May 5, 2017

(86) PCT No.: PCT/US2017/031212
§ 371 (c)(1),
(2) Date: Nov. 2, 2018

(87) PCT Pub. No.: WO2017/192945
PCT Pub. Date: Nov. 9, 2017

(65) Prior Publication Data
US 2019/0144941 A1     May 16, 2019

Related U.S. Application Data

(60) Provisional application No. 62/332,279, filed on May 5, 2016.

(51) Int. Cl.
| | | |
|---|---|---|
| C12Q 1/68 | (2018.01) | |
| C12P 19/34 | (2006.01) | |
| C12Q 1/6876 | (2018.01) | |
| C12Q 1/686 | (2018.01) | |

(52) U.S. Cl.
CPC ........... *C12Q 1/6876* (2013.01); *C12Q 1/686* (2013.01); *C12Q 2600/112* (2013.01); *C12Q 2600/118* (2013.01); *C12Q 2600/158* (2013.01)

(58) Field of Classification Search
CPC ............ C12Q 2600/158; C12Q 1/6876; C12Q 2600/118
See application file for complete search history.

(56) References Cited

U.S. PATENT DOCUMENTS

| 5,639,606 | A | 6/1997 | Willey |
| 6,812,023 | B1 | 11/2004 | Lamparski et al. |
| 6,899,863 | B1 | 5/2005 | Dhellin et al. |
| 7,198,923 | B1 | 4/2007 | Abrignani et al. |
| 2020/0199675 | A1 | 6/2020 | Hurley et al. |

FOREIGN PATENT DOCUMENTS

| WO | WO 2011/156763 A1 | 12/2011 |
| WO | WO 2014/107571 A1 | 7/2014 |
| WO | WO 2015/021158 A1 | 2/2015 |
| WO | WO 2016/007755 A1 | 1/2016 |
| WO | WO 2016/011383 A1 | 1/2016 |
| WO | WO 2016/054252 A1 | 4/2016 |
| WO | WO 2017/040515 A1 | 3/2017 |
| WO | WO 2017/192945 A1 | 11/2017 |
| WO | WO 2018/213392 A1 | 11/2018 |

OTHER PUBLICATIONS

Applied Biosystems by Life Technologies, User Guide, TaqMan OpenArray Pathway Panels (Nov. 5, 2013), 26 pages pritned form assets.fishersci.com. (Year: 2013).*
Hoshikawa, Y. et al. "Hypoxia induces different genes in the lungs of rats compared with mice" Physiol Genomics 12: 209-219 (Year: 2003).*
Li, M. et al. "Analysis of the RNA content of the exosomes derived from blood serum and urine and its potential as biomarkers" Phil. Trans. R. Soc. B 369: p. 1-7 (Year: 2014).*
Cheung, V.G. et al. "Natural variation in human gene expression assessed in lymphoblastoid cells" Nature Genetics, vol. 33, Mar. 2003, pp. 422-425. (Year: 2003).*
Assaker et al., "Discovery and Validation of a Urinary Exosome mRNA Signature for the Diagnosis of Human Kidney Transplant Rejection." Abstract #494, American Journal of Transplantation, American Transplant Congress, ATC 2018, vol. 18, Supplement 4, pp. 436-437.
Jackson et al., "Urinary Chemokines CXCL9 and CXCL10 Are Noninvasive Markers of Renal Allograft Rejection and BK Viral Infection." American Journal of Transplantation (2011); 11: 2228-2234.
Sigdel et al., "Perturbations in the urinary exosome in transplant rejection." Front Med (Lausanne) (2014); 1: 57; Published online Jan. 5, 2015, 10 pages; doi: 10.3389/fmed.2014.00057.
Tatapudi et al., "Noninvasive detection of renal allograft inflammation by measurements of mRNA for IP-10 and CXCR3 in urine." Kidney International (2004); 65:2390-2397.
Zhang et al., "mRNA Transcript Profiles of 14 Genes in Plasma Exosome Predict Risk for Antibody-Mediated Rejection (ABMR) of Renal Allografts." Abstract #23, American Journal of Transplantation, American Transplant Congress, ATC 2018, vol. 18, Supplement 4, 1 page.
Al-Nedawi, et al., "Intercellular transfer of the oncogenic receptor EGFRvIII by microvesicles derived from tumour cells." Nat Cell Biol. (2008); 10(5): 619-624.
Alvarez, S. et al., "Urinary exosomes as a source of kidney dysfunction biomarker in renal transplantation," Transplant Proc. (2013); 45(10): 3719-3723,.

(Continued)

*Primary Examiner* — Stephen T Kapushoc
(74) *Attorney, Agent, or Firm* — Ivor R. Elrifi; Matthew Pavao; Cooley LLP

(57) ABSTRACT

The invention relates generally to the use of microvesicle RNA signatures for diagnosis, predicting, and/or to monitor treatment efficacy, including patients who are candidates for renal transplant and/or who have received a renal transplant.

2 Claims, 16 Drawing Sheets

(56) References Cited

OTHER PUBLICATIONS

Balzar, et al., "The biology of the 17-1A antigen (Ep-CAM)." J Mol Med. (1999); 77(10): 699-712.
Brock, G. et al. "Liquid Biopsy for cancer screening, patient stratification and monitoring," Translational Cancer Center Research, (2015); 4(3): 280-290.
Chen, et al., "Microfluidic isolation and transcriptome analysis of serum microvesicles." Lab Chip (2010); 10(4): 505-511.
Cheruvanky, et al., "Rapid isolation of urinary exosomal biomarkers using a nanomembrane ultrafiltration concentrator," Am J Physiol Renal Physiol. (2007); 292: F1657-F1661.
Enderle et al., "Characterization of RNA from Exosomes and other Extracellular Vesicles Isolated by a Novel Spin Column-Based Method", PLOS One; Aug. 28, 2015, pp. 1-19; vol. No. 8, United States.
Hahn, "Molecular biology of double-minute chromosomes." BioEssays (1993); 15(7): 477-484.
Harada et al., "Non-Invasive Diagnosis of Post Kidney Transplant Complications by Urinary Exosomal mRNA Analysis." Meeting Abstracts, (May 4, 2015), Retrieved on Feb. 1, 2019, 15(7); 477-484.
International Preliminary Report on Patentability for International Application No. PCT/US2017/031212, dated Nov. 6, 2018, 6 pages.
International Search Report and Written Opinion for International Application No. PCT/US2017/031212, dated Nov. 11, 2017, 8 pages.
Miranda, et al., "Nucleic acids within urinary exosomes/microvesicles are potential biomarkers for renal disease." Kidney International (2010); 78(2): 191-199.
Murakami, T. et al., "Development of glomerulus-, tuble-, and collecting duct-specific mRNA assay in human urinary exosomes and microvesicles," PLoS One, Public Library of Science (2014); 9(9): 10 pages.
Nilsson, et al., "Prostate cancer-derived urine exosomes: a novel approach to biomarkers for prostate cancer." British Journal of Cancer (2009); 100: 1603-1607.
Raposo, et al., "B lymphocytes secrete antigen-presenting vesicles." Journal of Experimental Medicine (1996); 183: 1161-1172.
Skog, et al., "Glioblastoma microvesicles transport RNA and proteins that promote tumour growth and provide diagnostic biomarkers." Nature Cell Biology (2008); 10(12): 1470-1476.
Taylor and Gercel-Taylor, "MicroRNA signatures of tumor-derived exosomes as diagnostic biomarkers of ovarian cancer." Gynecol Oncol. (2008); 110: 13-21.
Went et al., "Frequent epcam protein expression in human carcinomas." Hum Pathol., 35:122-128 (2004).
Afaneh et al., "Urinary Cell Levels of mRNA for OX40, OX40L, PD-1, PD-L1, or PD-L2 and Acute Rejection of Human Renal Allografts," Transplantation, 90:1381-1387 (2010).
Akalin et al., "Gene expression analysis in human renal allograft biopsy samples using high-density oligoarray technology," Transplantation, 72(5):948-953 (2001).
Bloom et al., "Cell-Free DNA and Active Rejection in Kidney Allografts," J Am Soc Nephrol, 28:2221-2232 (2017). doi: https://doi.org/10.1681/ASN.2016091034.
Chen et al., "Differentially Expressed RNA from Public Microarray Data Identifies Serum Protein Biomarkers for Cross-Organ Transplant Rejection and Other Conditions," PLoS Comput Biol 6(9):e1000940 (2010), 12 pages. doi:10.1371/journal.pcbi.1000940.

Christakoudi et al., "Development of a multivariable gene-expression signature targeting T-cell-mediated rejection in peripheral blood of kidney transplant recipients validated in cross-sectional and longitudinal samples," EBioMedicine, 41:571-583 (2019).
Colvin, "Antibody-Mediated Renal Allograft Rejection: Diagnosis and Pathogenesis," J Am Soc Nephrol, 18:1046-1056 (2007). doi: 10.1681/ASN.2007010073.
Gielis et al., "Cell-Free DNA: An Upcoming Biomarker in Transplantation," American Journal of Transplantation, 15:2541-2551 (2015).
Gonzales et al., "Large-Scale Proteomics and Phosphoproteomics of Urinary Exosomes," J Am Soc Nephrol, 20:363-379 (2009), with Supplementary Table 1, 58 pages, doi: 10.1681/ASN.2008040406.
Grimm et al., "Clinical Rejection Is Distinguished from Subclinical Rejection by Increased Infiltration by a Population of Activated Macrophages," J Am Spc Nephrol, 10:1582-1589 (1999).
Hricik et al., "Multicenter Validation of Urinary CXCL9 as a Risk-Stratifying Biomarker for Kidney Transplant Injury," American Journal of Transplantation, 3:2634-2644 (2013).
Huang et al., "Early clinical experience using donor-derived cell-free DNA to detect rejection in kidney transplant recipients," Am J Transplant, 19:1663-1670 (2019).
Lim et al., "Novel urinary exosomal biomarkers of acute T cell-mediated rejection in kidney transplant recipients: A cross-sectional study," PLoS ONE, 13(9):e0204204, 17 pages. https://doi.org/10.1371/journal.pone.0204204.
Manfro et al., "Noninvasive Tim-3 Messenger RNA Evaluation in Renal Transplant Recipients With Graft Dysfunction," Transplantation, 86:1869-1874 (2008).
Martínez-Fernandez et al., "RNA Detection in Urine From RNA Extraction to Good Normalizer Molecules," The Journal of Molecular Diagnostics, 18(1): 15-22 (2016).
Muthukumar et al., "Messenger RNA for FOXP3 in the Urine of Renal-Allograft Recipients," N Engl J Med, 353:2342-51 (2005).
Orandi et al., "Quantifying Renal Allograft Loss Following Early Antibody-Mediated Rejection," American Journal of Transplantation, 15:489-498 (2015).
Park et al., "Integrated Kidney Exosome Analysis for the Detection of Kidney Transplant Rejection," ACS Nano, 11:11041-11046 (2017).
Pisitkun et al., "Identification and proteomic profiling of exosomes in human urine," PNAS, 101(36):13368-13373 (2004).
Sigdel et al., "Optimizing Detection of Kidney Transplant Injury by Assessment of Donor-Derived Cell-Free DNA via Massively Multiplex PCR," J. Clin. Med., 8(19) (2019), 17 pages. doi:10.3390/jcm8010019.
Spivey et al., "Gene expression profiling in acute allograft rejection: challenging the immunologic constant of rejection hypothesis," Journal of Translational Medicine, 9(174) (2011), 22 pages. http://www.translational-medicine.com/content/9/1/174.
Sreekumar et al., "Differential Allograft Gene Expression in Acute Cellular Rejection and Recurrence of Hepatitis C After Liver Transplantation," Liver Transpl, 8:814-821 (2002).
Suthanthiran et al., "Urinary-Cell mRNA Profile and Acute Cellular Rejection in Kidney Allografts," N Engl J Med, 369:20-31 (2013). doi:10.1056/NEJMoa1215555.
Wu et al., "Single-Cell Transcriptomics of a Human Kidney Allograft Biopsy Specimen Defines a Diverse Inflammatory Response," J Am Soc Nephrol, 29:2069-2080 (2018), and Supplementary Information, 15 pages, doi: https://doi.org/10.1681/ASN.2018020125.
Yang et al., "A urine score for noninvasive accurate diagnosis and prediction of kidney transplant rejection," Sci. Transl. Med., 12:eaba2501 (2020), 11 pages.

* cited by examiner

UBC

RPLP0

ACTB

PPIS

GAPDH

PGK1

B2M

Cycle Number

Raw Crt Values

Crt deltaCt Control Normalized

Crt

Urine collection → exoRNA extraction → RNA profiling

Blue bars        Red bars

FIGURE 12C

| Gene ID | Gene Name |
|---|---|
| CXCL9 | chemokine (C-X-C motif) ligand 9 |
| IFNGR1 | interferon gamma receptor 1 |
| CXCL10 | chemokine (C-X-C motif) ligand 10 |
| PXMP2 | peroxisomal membrane protein 2, 22kDa |
| TNFRSF19 | tumor necrosis factor receptor superfamily, member 19 |
| IL32 | interleukin 32 |
| AGTR1 | angiotensin II receptor, type 1 |
| EPHX2 | epoxide hydrolase 2, cytoplasmic |
| PDE4A | phosphodiesterase 4A, cAMP-specific |
| IRAK2 | interleukin-1 receptor-associated kinase 2 |
| IL22RA1 | interleukin 22 receptor, alpha 1 |
| IL1RAP | interleukin 1 receptor accessory protein |
| CXCL13 | chemokine (C-X-C motif) ligand 13 |
| CXCL6 | chemokine (C-X-C motif) ligand 6 |
| PTGES | prostaglandin E synthase |
| STAT1 | signal transducer and activator of transcription 1, 91kDa |
| TSLP | thymic stromal lymphopoietin |
| BMP7 | bone morphogenetic protein 7 |
| IL15RA | interleukin 15 receptor, alpha |
| CCL8 | chemokine (C-C motif) ligand 8 |
| PYCARD | PYD and CARD domain containing |
| C3 | complement component 3 |
| ZMYND15 | zinc finger, MYND-type containing 15 |

Blue bars                           Red bars

FIGURE 13C

| Gene ID | Gene Name |
|---|---|
| IL32 | interleukin 32 |
| IL15RA | interleukin 15 receptor, alpha |
| CXCL9 | chemokine (C-X-C motif) ligand 9 |
| PXMP2 | peroxisomal membrane protein 2, 22kDa |
| CXCL10 | chemokine (C-X-C motif) ligand 10 |
| C1R | complement component 1, r subcomponent |
| TNFRSF19 | tumor necrosis factor receptor superfamily, member 19 |
| CXCL14 | chemokine (C-X-C motif) ligand 14 |
| C3 | complement component 3 |
| PYCARD | PYD and CARD domain containing |
| IL1F5 | Interleukin 36 receptor antagonist |
| LEP | leptin |
| C7 | complement component 7 |
| FABP4 | fatty acid binding protein 4, adipocyte |
| CXCL6 | chemokine (C-X-C motif) ligand 6 |
| CD55 | CD55 molecule, decay accelerating factor for complement (Cromer blood group) |
| KRT1 | keratin 1 |
| BMP7 | bone morphogenetic protein 7 |
| INHBA | inhibin, beta A |
| IL1F8 | Interleukin 36, beta |
| PTGES | prostaglandin E synthase |
| EREG | epiregulin |
| IL12A | interleukin 12A (natural killer cell stimulatory factor 1, cytotoxic lymphocyte maturation factor 1, p35) |

PROFILING MICROVESICLE NUCLEIC ACIDS AND USES THEREOF AS SIGNATURES IN DIAGNOSIS OF RENAL TRANSPLANT REJECTION

RELATED APPLICATIONS

This application is a U.S. National Phase Application, filed under 35 U.S.C. 371, of International Application No. PCT/US2017/031212, filed on May 5, 2017, which claims priority to, and the benefit of, U.S. Provisional Application No. 62/332,279, filed May 5, 2016; the contents of each of which are incorporated herein by reference in their entirety.

FIELD OF THE INVENTION

The invention relates generally to the use of microvesicle RNA signatures for diagnosis, predicting, and/or to monitor treatment efficacy in patients, e.g., patients who are candidates for renal transplant and/or who have received a renal transplant.

BACKGROUND

Increasing knowledge of the genetic and epigenetic changes occurring in cells provides an opportunity to detect, characterize, and monitor diseases and disorders by analyzing disease-specific nucleic acid sequences and profiles. These changes can be observed by detecting any of a variety of disease-related biomarkers. Various molecular diagnostic assays are used to detect these biomarkers and produce valuable information for patients, doctors, clinicians and researchers.

The ability to perform these tests using a bodily fluid sample has wide ranging implications in terms of patient welfare, the ability to conduct longitudinal disease monitoring, and the ability to obtain expression profiles even when tissue cells are not easily accessible.

Accordingly, there exists a need for new, noninvasive methods of detecting biomarkers, for example, biomarkers in microvesicles, to aid in diagnosis, prognosis, monitoring, or therapy selection for a disease or other medical condition.

SUMMARY OF THE INVENTION

The disclosure provides methods for the use of microvesicle RNA signatures to monitor treatment efficacy and/or to predict kidney rejection in a subject. In some embodiments, the methods are used to monitor treatment efficacy longitudinally.

The methods and compositions provided herein are useful for measuring nucleic acids obtained from microvesicles, e.g., microvesicle RNA, also referred to herein as exosome RNA or exosomal RNA, as a diagnostic for transplant rejection such as, for example, kidney transplant rejection.

Prior to the instant methods, nucleic acid signatures were obtained from cells in a urine sample. As shown in the studies presented herein, the cells in a urine sample and the nucleic acids from the microvesicle fraction of the urine sample were analyzed in parallel. Interestingly, the cells in urine were not able to reliably and successfully discriminate between patients who experienced kidney transplant rejection, and those who did not experience any rejection symptoms or other indications. In contrast, the nucleic acid signatures derived from the microvesicles reliably and successfully discriminated between these two groups.

Traditionally, biomarker discovery and development has required the use of material obtained from tissue biopsies. However, recent developments in the exosome field have allowed biomarker research in biofluids to evolve. Exosomes are highly stable microvesicles, approximately 30-200 nm in diameter, that are shed by cells into all biofluids, including blood, urine, and cerebrospinal fluid, carrying a rich source of intact protein and RNA. Exosomes and other vesicles can be released by multi-vesicular body pathway or through direct budding at the plasma membrane. RNA can be efficiently isolated and addressed using technologies such as RT-qPCR and NGS (see e.g., Brock, G. et al. (2015) Liquid biopsy for cancer screening, patient stratification and monitoring. Translational Cancer Research, 4(3), 280-290; and Enderle, D. et al. (2015) Characterization of RNA from Exosomes and Other Extracellular Vesicles Isolated by a Novel Spin Column-Based Method. PLoS ONE, 10(8): e0136133. doi:10.1371/journal.pone.0136133).

In some embodiments, the methods and kits described herein isolate the microvesicle fraction by capturing the microvesicles to a surface and subsequently lysing the microvesicles to release the nucleic acids, particularly RNA, contained therein. The methods and kits provided herein isolate the microvesicle fraction using any suitable technique. In some embodiments, the microvesicles are isolated using the methods and capture surfaces described in PCT Publication No. WO 2014/107571 and in PCT Publication No. WO 2016/007755, the contents of each of which are hereby incorporated by reference in their entirety. In some embodiments, the microvesicles are isolated from a urine sample using the methods and capture surfaces described in PCT Publication No. WO 2015/021158, the contents of which are hereby incorporated by reference in their entirety.

The present disclosure provides methods of detecting one or more biomarkers in a biological sample to aid in diagnosis, prognosis, monitoring, or therapy selection for transplant rejection such as, for example, kidney transplant rejection. The methods and kits provided herein are useful in detecting one or more biomarkers from the microvesicle fraction of a biological sample, e.g., a urine sample.

The biological sample used in the methods provided herein is a bodily fluid. The bodily fluids can be fluids isolated from anywhere in the body of the subject, preferably a peripheral location, including but not limited to, for example, urine, blood, plasma, serum, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. For example, the bodily fluid is urine, blood, plasma, serum, or cerebrospinal fluid. In some embodiments, the bodily fluid is urine.

In any of the foregoing methods, the nucleic acids are DNA or RNA. Examples of RNA include messenger RNAs, transfer RNAs, ribosomal RNAs, small RNAs (non-protein-coding RNAs, non-messenger RNAs), microRNAs, piRNAs, exRNAs, snRNAs and snoRNAs. In some embodiments, the RNA is miRNA.

In any of the foregoing methods, the nucleic acids are isolated from or otherwise derived from a microvesicle fraction. In some embodiments, the nucleic acids are RNA or DNA or RNA and DNA isolated from or otherwise derived from a microvesicle fraction. In some embodiments, the nucleic acids are RNA isolated from or otherwise derived from a microvesicle fraction.

In any of the foregoing methods, the nucleic acids are cell-free nucleic acids, also referred to herein as circulating nucleic acids. In some embodiments, the cell-free nucleic acids are DNA or RNA. In some embodiments, the cell-free nucleic acid is cell-free DNA.

In some embodiments, the capture surface is positively charged. In another embodiment, the capture surface is negatively charged. In yet another embodiment, the capture surface is neutral.

In some embodiments, the capture surface is a membrane. In some embodiments, the capture surface is a bead. For example, the bead is magnetic. Alternatively, the bead is non-magnetic. In yet another embodiment, the bead is functionalized with an affinity ligand.

In some embodiments, control particles may be added to the sample prior to microvesicle isolation and/or nucleic acid extraction to serve as an internal control to evaluate the efficiency or quality of microvesicle purification and/or nucleic acid extraction. The methods described herein provide for the efficient isolation and the control particles along with the microvesicle fraction. These control particles include Q-beta bacteriophage, virus particles, or any other particle that contains control nucleic acids (e.g., at least one control target gene) that may be naturally occurring or engineered by recombinant DNA techniques. In some embodiments, the quantity of control particles is known before the addition to the sample. The control target gene can be quantified using real-time PCR analysis. Quantification of a control target gene can be used to determine the efficiency or quality of the microvesicle purification or nucleic acid extraction processes.

In some embodiments, the methods and kits described herein include one or more in-process controls. In some embodiments, the in-process control is detection and analysis of a reference gene that indicates plasma quality (i.e., an indicator of the quality of the plasma sample). In some embodiments, the reference gene(s) is/are a plasma-inherent transcript. In some embodiments, the reference gene(s) is/are analyzed by additional qPCR.

In some embodiments, the extracted nucleic acids are subject to further analysis. Various nucleic acid sequencing techniques are used to detect and analyze nucleic acids such as cell free DNA and/or RNA extracted from the microvesicle fraction from biological samples. Analysis of nucleic acids such as cell free DNA and/or nucleic acids extracted from microvesicles for diagnostic purposes has wide-ranging implications due to the non-invasive nature in which microvesicles can be easily collected.

Various aspects and embodiments of the invention will now be described in detail. It will be appreciated that modification of the details may be made without departing from the scope of the invention. Further, unless otherwise required by context, singular terms shall include pluralities and plural terms shall include the singular.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representations as to the contents of these documents are based on the information available to the applicants and do not constitute any admission as to the correctness of the dates or contents of these documents.

BRIEF DESCRIPTION OF THE FIGURES

FIG. 5 depicts all samples, while FIG. 6 depicts the microvesicle only sample.

FIG. 8 is the plot for all samples tested,

FIG. 9 is the plot for only the cell pellet samples, and

FIG. 10 is the plot for only the microvesicle samples. The two outliers shown in FIG. 10 have been accounted for: in E10, the subject had allergic interstitial nephritis (AIN), which can lead to an ambiguous diagnosis; and in E19, the sample was of a low quality.

FIGS. 12A, 12B, and 12C are a series of a graph, an illustration, and a table depicting the gene signature identified in training cohort differentiating between kidney rejection and non-rejection. In the Boxplot of FIG. 12A, the height of each bar is the rejection probability estimated from gene-expression (Red bars—rejection samples, blue bars—non-rejection samples). In the Heatmap of FIG. 12B, marker expression levels (blue tones indicate higher Crt values relative to quantile normalization value, and thus lower relative expression levels).

FIGS. 13A, 13B, and 13C are a series of a graph, an illustration, and a table depicting the performance of 23-gene signature in test cohort. In the Boxplot of FIG. 13A, the height of each bar is the rejection probability estimated (Red bars—rejection samples, blue bars—non-rejection samples). In the Heatmap of FIG. 13B, marker expression levels (blue tones indicate higher Crt values relative to quantile normalization value, and thus lower relative expression levels).

DETAILED DESCRIPTION OF THE INVENTION

Figure 1:
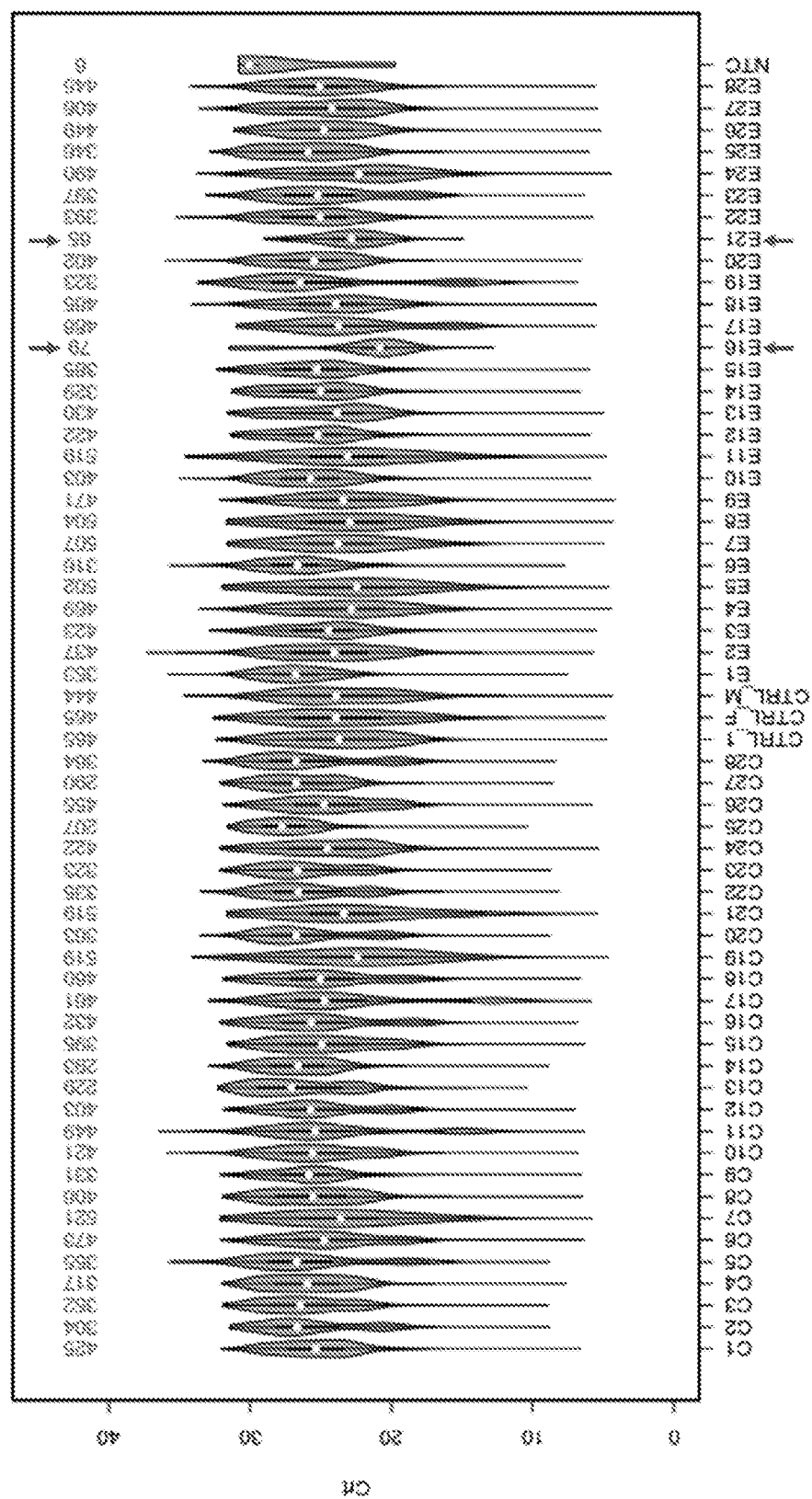
FIG. 1 is a graph depicting the raw data from all assays, with 607 assays for each sample. The numbers at the top of the figure (i.e., 425, 304, 352, . . . 406, 445, 6) are the number of assays out of 607 with readout. E16 and E21 failed, and the rest ranged from 34% to 86%. The width in each violin plot reflects the number of data points, where the abbreviation C## used on the X-axis represents the cell pellet samples, and the abbreviation E## used on the X-axis represents the microvesicle samples.

The disclosure provides methods for the use of microvesicle RNA signatures to monitor treatment efficacy and/or to predict treatment efficacy. In some embodiments, the methods are used to monitor treatment efficacy longitudinally.

The methods and compositions provided herein are useful for measuring nucleic acids obtained from microvesicles, e.g., microvesicle RNA, also referred to herein as exosome RNA or exosomal RNA, as a diagnostic for transplant rejection such as, for example, kidney transplant rejection.

As used herein, the term "nucleic acids" refer to DNA and RNA. The nucleic acids can be single stranded or double stranded. In some instances, the nucleic acid is DNA. In some instances, the nucleic acid is RNA. RNA includes, but is not limited to, messenger RNA, transfer RNA, ribosomal RNA, non-coding RNAs, microRNAs, and HERV elements.

As used herein, the term "biological sample" refers to a sample that contains biological materials such as DNA, RNA and protein.

In some embodiments, the biological sample may suitably comprise a bodily fluid from a subject. The bodily fluids can be fluids isolated from anywhere in the body of the subject, such as, for example, a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid and cell culture supernatant, and combinations thereof. Biological samples can also include fecal or cecal samples, or supernatants isolated therefrom.

In some embodiments, the biological sample may suitably comprise cell culture supernatant.

In some embodiments, the biological sample may suitably comprise a tissue sample from a subject. The tissue sample can be isolated from anywhere in the body of the subject.

A suitable sample volume of a bodily fluid is, for example, in the range of about 0.1 ml to about 30 ml fluid. The volume of fluid may depend on a few factors, e.g., the type of fluid used. For example, the volume of serum samples may be about 0.1 ml to about 4 ml, preferably about 0.2 ml to 4 ml. The volume of plasma samples may be about 0.1 ml to about 4 ml, preferably 0.5 ml to 4 ml. The volume of urine samples may be about 10 ml to about 30 ml, preferably about 20 ml.

While the examples provided herein used plasma samples, the skilled artisan will appreciate that these methods are applicable to a variety of biological samples. Other suitable biological samples include urine, cerebrospinal fluid, blood including blood components, e.g., plasma and serum, sputum, pleural fluid, nipple aspirates, lymph fluid, fluid of the respiratory, intestinal, and genitourinary tracts, tear fluid, saliva, breast milk, fluid from the lymphatic system, semen, intraorgan system fluid, ascitic fluid, tumor cyst fluid, amniotic fluid, cell culture supernatant and combinations thereof.

The methods and kits of the disclosure are suitable for use with samples derived from a human subject. The methods and kits of the disclosure are suitable for use with samples derived from a human subject. In addition, the methods and kits of the disclosure are also suitable for use with samples derived from a human subject. The methods and kits of the disclosure are suitable for use with samples derived from a non-human subject such as, for example, a rodent, a non-human primate, a companion animal (e.g., cat, dog, horse), and/or a farm animal (e.g., chicken).

The term "subject" is intended to include all animals shown to or expected to have nucleic acid-containing particles. In particular embodiments, the subject is a mammal, a human or nonhuman primate, a dog, a cat, a horse, a cow, other farm animals, or a rodent (e.g. mice, rats, guinea pig, etc.). A human subject may be a normal human being without observable abnormalities, e.g., a disease. A human subject may be a human being with observable abnormalities, e.g., a disease. The observable abnormalities may be observed by the human being himself, or by a medical professional. The term "subject," "patient," and "individual" are used interchangeably herein.

While the working examples provided herein use a membrane as the capture surface, it should be understood that the format of the capturing surface, e.g., beads or a filter (also referred to herein as a membrane), does not affect the ability of the methods provided herein to efficiently capture microvesicles from a biological sample.

A wide range of surfaces are capable of capturing microvesicles according to the methods provided herein, but not all surfaces will capture microvesicles (some surfaces do not capture anything).

The present disclosure also describes a device for isolating and concentrating microvesicles from biological or clinical samples using disposable plastic parts and centrifuge equipment. For example, the device comprises a column comprising a capture surface (i.e., a membrane filter), a holder that secures the capture surface between the outer frit and an inner tube, and a collection tube. The outer frit comprises a large net structure to allow passing of liquid, and is preferably at one end of the column. The inner tube holds the capture surface in place, and preferably is slightly conus-shaped. The collection tube may be commercially available, i.e., 50 ml Falcon tube. The column is preferably suitable for spinning, i.e., the size is compatible with standard centrifuge and micro-centrifuge machines.

In embodiments where the capture surface is a membrane, the device for isolating the microvesicle fraction from a biological sample contains at least one membrane. In some embodiments, the device comprises one, two, three, four, five or six membranes. In some embodiments, the device comprises three membranes. In embodiments where the device comprises more than one membrane, the membranes are all directly adjacent to one another at one end of the column. In embodiments where the device comprises more than one membrane, the membranes are all identical to each other, i.e., are of the same charge and/or have the same functional group.

It should be noted that capture by filtering through a pore size smaller than the microvesicles is not the primary mechanism of capture by the methods provided herein. However, filter pore size is nevertheless very important, e.g. because mRNA gets stuck on a 20 nm filter and cannot be recovered, whereas microRNAs can easily be eluted off, and e.g. because the filter pore size is an important parameter in available surface capture area.

The methods provided herein use any of a variety of capture surfaces. In some embodiments, the capture surface is a membrane, also referred to herein as a filter or a membrane filter. In some embodiments, the capture surface is a commercially available membrane. In some embodiments, the capture surface is a charged commercially available membrane. In some embodiments, the capture surface is neutral. In some embodiments, the capture surface is selected from Mustang® Ion Exchange Membrane from PALL Corporation; Vivapure® Q membrane from Sartorius AG; Sartobind Q, or Vivapure® Q Maxi H; Sartobind® D from Sartorius AG, Sartobind (S) from Sartorius AG, Sartobind® Q from Sartorius AG, Sartobind® IDA from Sartorius AG, Sartobind® Aldehyde from Sartorius AG, Whatman® DE81 from Sigma, Fast Trap Virus Purification column from EMD Millipore; Thermo Scientific* Pierce Strong Cation and Anion Exchange Spin Columns.

In embodiments where the capture surface is charged, the capture surface can be a charged filter selected from the group consisting of 0.65 um positively charged Q PES vacuum filtration (Millipore), 3-5 um positively charged Q RC spin column filtration (Sartorius), 0.8 um positively charged Q PES homemade spin column filtration (Pall), 0.8 um positively charged Q PES syringe filtration (Pall), 0.8 um negatively charged S PES homemade spin column filtration (Pall), 0.8 um negatively charged S PES syringe filtration (Pall), and 50 nm negatively charged nylon syringe filtration (Sterlitech). Preferably, the charged filter is not housed in a syringe filtration apparatus, as Qiazol/RNA is harder to get out of the filter in these embodiments. Preferably, the charged filter is housed at one end of a column.

In embodiments where the capture surface is a membrane, the membrane can be made from a variety of suitable materials. In some embodiments, the membrane is polyethersulfone (PES) (e.g., from Millipore or PALL Corp.). In some embodiments, the membrane is regenerated cellulose (RC) (e.g., from Sartorius or Pierce).

In some embodiments, the capture surface is a positively charged membrane. In some embodiments, the capture surface is a Q membrane, which is a positively charged membrane and is an anion exchanger with quaternary amines. For example, the Q membrane is functionalized with quaternary ammonium, $R-CH_2-N^+(CH_3)_3$. In some embodiments, the capture surface is a negatively charged membrane. In some embodiments, the capture surface is an S membrane, which is a negatively charged membrane and is a cation exchanger with sulfonic acid groups. For example, the S membrane is functionalized with sulfonic acid, $R-CH_2-SO_3^-$. In some embodiments, the capture surface is a D membrane, which is a weak basic anion exchanger with diethylamine groups, $R-CH_2-NH^+(C_2H_5)_2$. In some embodiments, the capture surface is a metal chelate membrane. For example, the membrane is an IDA membrane, functionalized with minodiacetic acid $-N(CH_2COOH^-)_2$. In some embodiments, the capture surface is a microporous membrane, functionalized with aldehyde groups, $-CHO$. In other embodiments, the membrane is a weak basic anion exchanger, with diethylaminoethyl (DEAE) cellulose. Not all charged membranes are suitable for use in the methods provided herein, e.g., RNA isolated using Sartorius Vivapure S membrane spin column showed RT-qPCR inhibition and, thus, unsuitable for PCR related downstream assay.

In embodiments where the capture surface is charged, microvesicles can be isolated with a positively charged filter.

In embodiments where the capture surface is charged, the pH during microvesicle capture is a pH≤7. In some embodiments, the pH is greater than 4 and less than or equal to 8.

Depending on the membrane material, the pore sizes of the membrane range from 3 μm to 20 nm.

The surface charge of the capture surface can be positive, negative or neutral. In some embodiments, the capture surface is a positively charged bead or beads.

The methods provided herein include a lysis reagent. In some embodiments, the agent used for on-membrane lysis is a phenol-based reagent. In some embodiments, the lysis reagent is a guanidinium-based reagent. In some embodiments, the lysis reagent is a high salt based buffer. In some embodiments, the lysis reagent is QIAzol.

In some embodiments, the methods include one or more wash steps, for example, after contacting the biological sample with the capture surface. In some embodiments, detergents are added to the wash buffer to facilitate removing the non-specific binding (i.e., contaminants, cell debris, and circulating protein complexes or nucleic acids), to obtain a more pure microvesicle fraction. Detergents suitable for use include, but are not limited to, sodium dodecyl sulfate (SDS), Tween-20, Tween-80, Triton X-100, Nonidet P-40 (NP-40), Brij-35, Brij-58, octyl glucoside, octyl thioglucoside, CHAPS or CHAPSO.

In some embodiments, the capture surface, e.g., membrane, is housed within a device used for centrifugation; e.g. spin columns, or for vacuum system e.g. vacuum filter holders, or for filtration with pressure e.g. syringe filters. In a preferred embodiment, the capture surface is housed in a spin column or vacuum system.

The isolation of microvesicles from a biological sample prior to extraction of nucleic acids is advantageous for the following reasons: 1) extracting nucleic acids from microvesicles provides the opportunity to selectively analyze disease or tumor-specific nucleic acids obtained by isolating disease or tumor-specific microvesicles apart from other microvesicles within the fluid sample; 2) nucleic acid-containing microvesicles produce significantly higher yields of nucleic acid species with higher integrity as compared to the yield/integrity obtained by extracting nucleic acids directly from the fluid sample without first isolating microvesicles; 3) scalability, e.g., to detect nucleic acids expressed at low levels, the sensitivity can be increased by concentrating microvesicles from a larger volume of sample using the methods described herein; 4) more pure or higher quality/integrity of extracted nucleic acids in that proteins, lipids, cell debris, cells and other potential contaminants and PCR inhibitors that are naturally found within biological samples are excluded before the nucleic acid extraction step; and 5) more choices in nucleic acid extraction methods can be utilized as isolated microvesicle fractions can be of a smaller volume than that of the starting sample volume, making it possible to extract nucleic acids from these fractions or pellets using small volume column filters.

Several methods of isolating microvesicles from a biological sample have been described in the art. For example, a method of differential centrifugation is described in a paper by Raposo et al. (Raposo et al., 1996), a paper by Skog et. al. (Skog et al., 2008) and a paper by Nilsson et. al. (Nilsson et al., 2009). Methods of ion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel Taylor (Taylor and Gercel-Taylor, 2008). A method of nanomembrane ultrafiltration concentration is described in a paper by Cheruvanky et al. (Cheruvanky et al., 2007). A method of Percoll gradient isolation is described in a publication by Miranda et al. (Miranda et al., 2010). Further, microvesicles may be identified and isolated from bodily fluid of a subject by a microfluidic device (Chen et al., 2010). In research and development, as well as commercial applications of nucleic acid biomarkers, it is desirable to extract high quality nucleic acids from biological samples in a consistent, reliable, and practical manner.

In some embodiments, the sample is not pre-processed prior to isolation and extraction of nucleic acids, e.g., DNA and/or DNA and RNA, from the biological sample.

In some embodiments, the sample is subjected to a pre-processing step prior to isolation, purification or enrichment of the microvesicles is performed to remove large unwanted particles, cells and/or cell debris and other contaminants present in the biological sample. The pre-processing steps may be achieved through one or more centrifugation steps (e.g., differential centrifugation) or one or more filtration steps (e.g., ultrafiltration), or a combination thereof. Where more than one centrifugation pre-processing steps are performed, the biological sample may be centrifuged first at the lower speed and then at the higher speed. If desired, further suitable centrifugation pre-processing steps may be carried out. Alternatively or in addition to the one or more centrifugation pre-processing steps, the biological sample may be filtered. For example, a biological sample may be first centrifuged at 20,000 g for 1 hour to remove large unwanted particles; the sample can then be filtered, for example, through a 0.8 μm filter.

In some embodiments, the sample is pre-filtered to exclude particles larger than 0.8 μm. In some embodiments, the sample includes an additive such as EDTA, sodium citrate, and/or citrate-phosphate-dextrose.

In some embodiments, one or more centrifugation steps are performed before or after contacting the biological sample with the capture surface to separate microvesicles and concentrate the microvesicles isolated from the biological fraction. For example, the sample is centrifuged at 20,000 g for 1 hour at 4° C. To remove large unwanted particles, cells, and/or cell debris, the samples may be centrifuged at a low speed of about 100-500 g, preferably about 250-300 g. Alternatively or in addition, the samples may be centrifuged at a higher speed. Suitable centrifugation speeds are up to about 200,000 g; for example from about 2,000 g to less than about 200,000 g. Speeds of above about 15,000 g and less than about 200,000 g or above about 15,000 g and less than about 100,000 g or above about 15,000 g and less than about 50,000 g are preferred. Speeds of from about 18,000 g to about 40,000 g or about 30,000 g; and from about 18,000 g to about 25,000 g are more preferred. Particularly preferred is a centrifugation speed of about 20,000 g. Generally, suitable times for centrifugation are from about 5 minutes to about 2 hours, for example, from about 10 minutes to about 1.5 hours, or more preferably from about 15 minutes to about 1 hour. A time of about 0.5 hours may be preferred. It is sometimes preferred to subject the biological sample to centrifugation at about 20,000 g for about 0.5 hours. However the above speeds and times can suitably be used in any combination (e.g., from about 18,000 g to about 25,000 g, or from about 30,000 g to about 40,000 g for about 10 minutes to about 1.5 hours, or for about 15 minutes to about 1 hour, or for about 0.5 hours, and so on). The centrifugation step or steps may be carried out at below-ambient temperatures, for example at about 0-10° C., preferably about 1-5° C., e.g., about 3° C. or about 4° C.

In some embodiments, one or more filtration steps are performed before or after contacting the biological sample with the capture surface. A filter having a size in the range about 0.1 to about 1.0 μm may be employed, preferably about 0.8 μm or 0.22 μm. The filtration may also be performed with successive filtrations using filters with decreasing porosity.

In some embodiments, one or more concentration steps are performed, in order to reduce the volumes of sample to be treated during the chromatography stages, before or after contacting the biological sample with the capture surface. Concentration may be through centrifugation of the sample at high speeds, e.g. between 10,000 and 100,000 g, to cause the sedimentation of the microvesicles. This may consist of a series of differential centrifugations. The microvesicles in the pellet obtained may be reconstituted with a smaller volume and in a suitable buffer for the subsequent steps of the process. The concentration step may also be performed by ultrafiltration. In fact, this ultrafiltration both concentrates the biological sample and performs an additional purification of the microvesicle fraction. In another embodiment, the filtration is an ultrafiltration, preferably a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibers (Amicon, Millipore, Sartorius, Pall, GF, Sepracor). Within the scope of the invention, the use of membranes with a cut-off threshold below 1000 kDa, preferably between 100 kDa and 1000 kDa, or even more preferably between 100 kDa and 600 kDa, is advantageous.

In some embodiments, one or more size-exclusion chromatography step or gel permeation chromatography steps are performed before or after contacting the biological sample with the capture surface. To perform the gel permeation chromatography step, a support selected from silica, acrylamide, agarose, dextran, ethylene glycol-methacrylate co-polymer or mixtures thereof, e.g., agarose-dextran mixtures, are preferably used. For example, such supports include, but are not limited to: SUPERDEX® 200HR (Pharmacia), TSK G6000 (TosoHaas) or SEPHACRYL® S (Pharmacia).

In some embodiments, one or more affinity chromatography steps are performed before or after contacting the biological sample with the capture surface. Some microvesicles can also be characterized by certain surface molecules. Because microvesicles form from budding of the cell plasma membrane, these microvesicles often share many of the same surface molecules found on the cells they originated from. As used herein, "surface molecules" refers collectively to antigens, proteins, lipids, carbohydrates, and markers found on the surface or in or on the membrane of the microvesicle. These surface molecules can include, for example, receptors, tumor-associated antigens, membrane protein modifications (e.g., glycosylated structures). For example, microvesicles that bud from tumor cells often display tumor-associated antigens on their cell surface. As such, affinity chromatography or affinity exclusion chromatography can also be utilized in combination with the methods provided herein to isolate, identify, and or enrich for specific populations of microvesicles from a specific donor cell type (Al-Nedawi et al., 2008; Taylor and Gercel-Taylor, 2008). For example, tumor (malignant or non-malignant) microvesicles carry tumor-associated surface antigens and may be detected, isolated and/or enriched via these specific tumor-associated surface antigens. In one example, the surface antigen is epithelial cell adhesion molecule (EpCAM), which is specific to microvesicles from carcinomas of long, colorectal, breast, prostate, head and neck, and hepatic origin, but not of hematological cell origin (Balzar et al., 1999; Went et al., 2004). Additionally, tumor-specific microvesicles can also be characterized by the lack of certain surface markers, such as CD80 and CD86. In these cases, microvesicles with these markers may be excluded for further analysis of tumor specific markers, e.g., by affinity exclusion chromatography. Affinity chromatography can be accomplished, for example, by using different supports, resins, beads, antibodies, aptamers, aptamer analogs, molecularly imprinted polymers, or other molecules known in the art that specifically target desired surface molecules on microvesicles.

Optionally, control particles may be added to the sample prior to microvesicle isolation or nucleic acid extraction to serve as an internal control to evaluate the efficiency or quality of microvesicle purification and/or nucleic acid extraction. The methods described herein provide for the efficient isolation and the control particles along with the microvesicle fraction. These control particles include Q-beta bacteriophage, virus particles, or any other particle that contains control nucleic acids (e.g., at least one control target gene) that may be naturally occurring or engineered by recombinant DNA techniques. In some embodiments, the quantity of control particles is known before the addition to the sample. The control target gene can be quantified using real-time PCR analysis. Quantification of a control target gene can be used to determine the efficiency or quality of the microvesicle purification or nucleic acid extraction processes.

Preferably, the control particle is a Q-beta bacteriophage, referred to herein as "Q-beta particle." The Q-beta particle used in the methods described herein may be a naturally-occurring virus particle or may be a recombinant or engineered virus, in which at least one component of the virus particle (e.g., a portion of the genome or coat protein) is synthesized by recombinant DNA or molecular biology techniques known in the art. Q-beta is a member of the leviviridae family, characterized by a linear, single-stranded RNA genome that consists of 3 genes encoding four viral proteins: a coat protein, a maturation protein, a lysis protein, and RNA replicase. Due to its similar size to average microvesicles, Q-beta can be easily purified from a biological sample using the same purification methods used to isolate microvesicles, as described herein. In addition, the low complexity of the Q-beta viral single-stranded gene structure is advantageous for its use as a control in amplification-based nucleic acid assays. The Q-beta particle contains a control target gene or control target sequence to be detected or measured for the quantification of the amount of Q-beta particle in a sample. For example, the control target gene is the Q-beta coat protein gene. After addition of the Q-beta particles to the biological sample, the nucleic acids from the Q-beta particle are extracted along with the nucleic acids from the biological sample using the extraction methods described herein. Detection of the Q-beta control target gene can be determined by RT-PCR analysis, for example, simultaneously with the biomarker(s) of interest. A standard curve of at least 2, 3, or 4 known concentrations in 10-fold dilution of a control target gene can be used to determine copy number. The copy number detected and the quantity of Q-beta particle added can be compared to determine the quality of the isolation and/or extraction process.

In a preferred embodiment, the Q-beta particles are added to the urine sample prior to nucleic acid extraction. For example, the Q-beta particles are added to the urine sample prior to ultrafiltration and/or after the pre-filtration step.

In some embodiments, 50, 100, 150, 200, 250, 300, 350, 400, 450, 500, 1,000 or 5,000 copies of Q-beta particles added to a bodily fluid sample. In a preferred embodiment, 100 copies of Q-beta particles are added to a bodily fluid sample. The copy number of Q-beta particles can be calculated based on the ability of the Q-beta bacteriophage to infect target cells. Thus, the copy number of Q-beta particles is correlated to the colony forming units of the Q-beta bacteriophage.

Detection of Nucleic Acid Biomarkers

In some embodiments, the extracted nucleic acid comprises DNA and/or DNA and RNA. In embodiments where the extracted nucleic acid comprises DNA and RNA, the RNA is preferably reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first of reverse transcription to convert RNA into cDNA and a second step of quantifying the amount of cDNA using quantitative PCR. As demonstrated in the examples that follow, the RNAs extracted from nucleic acid-containing particles using the methods disclosed herein include many species of transcripts including, but not limited to, ribosomal 18S and 28S rRNA, microRNAs, transfer RNAs, transcripts that are associated with diseases or medical conditions, and biomarkers that are important for diagnosis, prognosis and monitoring of medical conditions.

For example, RT-PCR analysis determines a Ct (cycle threshold) value for each reaction. In RT-PCR, a positive reaction is detected by accumulation of a fluorescence signal. The Ct value is defined as the number of cycles required for the fluorescent signal to cross the threshold (i.e., exceeds background level). Ct levels are inversely proportional to the amount of target nucleic acid, or control nucleic acid, in the sample (i.e., the lower the Ct level, the greater the amount of control nucleic acid in the sample).

In another embodiment, the copy number of the control nucleic acid can be measured using any of a variety of art-recognized techniques, including, but not limited to, RT-PCR. Copy number of the control nucleic acid can be determined using methods known in the art, such as by generating and utilizing a calibration, or standard curve.

In some embodiments, one or more biomarkers can be one or a collection of genetic aberrations, which is used herein to refer to the nucleic acid amounts as well as nucleic acid variants within the nucleic acid-containing particles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

The analysis of nucleic acids present in the isolated particles is quantitative and/or qualitative. For quantitative analysis, the amounts (expression levels), either relative or absolute, of specific nucleic acids of interest within the isolated particles are measured with methods known in the art (described below). For qualitative analysis, the species of specific nucleic acids of interest within the isolated microvesicles, whether wild type or variants, are identified with methods known in the art.

The present invention also includes various uses of the new methods of isolating microvesicles from a biological sample for high quality nucleic acid extraction from a for (i) aiding in the diagnosis of a subject, (ii) monitoring the progress or reoccurrence of a disease or other medical condition in a subject, or (iii) aiding in the evaluation of treatment efficacy for a subject undergoing or contemplating treatment for a disease or other medical condition; wherein the presence or absence of one or more biomarkers in the nucleic acid extraction obtained from the method is determined, and the one or more biomarkers are associated with the diagnosis, progress or reoccurrence, or treatment efficacy, respectively, of a disease or other medical condition.

Kits for Isolating Microvesicles from a Biological Sample

One aspect of the present invention is further directed to kits for use in the methods disclosed herein. The kit comprises a capture surface apparatus sufficient to separate microvesicles from a biological sample from unwanted particles, debris, and small molecules that are also present in the biological sample. The present invention also optionally includes instructions for using the foregoing reagents in the isolation and optional subsequent nucleic acid extraction process.

EXAMPLES

While the examples provided herein use a variety of membranes and devices used for centrifugation and/or filtration purposes, it is to be understood that these methods can be used with any capture surface and/or housing device that allows for the efficient capture of microvesicles and release of the nucleic acids, particularly, RNA, contained therein.

Example 1: Pilot Study of Urinary Microvesicle Signature for the Diagnosis of Human Kidney Transplant Rejection The studies presented herein were run on a pilot of 28 patients, and as detailed herein, the microvesicle RNA signatures, also referred to herein as the urinary microvesicle RNA signature, the exosome RNA signature, and/or the urinary exosome RNA signature, perfectly clustered the patients with rejection. In the studies presented herein, the microvesicle RNA signature is a microvesicle mRNA signature.

In the studies presented herein, 28 samples from 24 patients were used. Four patients with two samples each for two visits were used. Each sample was processed to extract RNA from cellular fraction or microvesicle fraction. The demographics of the samples were as follows: eight female samples and 20 male samples. Fourteen patients had transplant rejection, and fourteen patients had no symptoms or other indication of transplant rejection. In addition, three in-house control samples were also used: one pooled male & female sample ("CTRL_1"), one pooled male sample ("CTRL_M"), and one pooled female sample ("CTRL_F").

A brief description of each subject is provided below in Table 1:

TABLE 1

| Sample info | | | | | | |
|---|---|---|---|---|---|---|
| Sample ID | Source | Sample ID | Source | Sex | Rejection | Note |
| E1 | urine microvesicles | C1 | urine cells | F | Yes | Antibody mediated rejection chronic |
| E2 | urine microvesicles | C2 | urine cells | M | Yes | Acute cellular rejection, IB |
| E3 | urine microvesicles | C3 | urine cells | M | No | No rejection, Acute tubular injury |
| E4 | urine microvesicles | C4 | urine cells | M | No | No rejection, Acute tubular injury |
| E5 | urine microvesicles | C5 | urine cells | M | No | No rejection |
| E6 | urine microvesicles | C6 | urine cells | M | No | No rejection |
| E7 | urine microvesicles | C7 | urine cells | M | Yes | Cellular rejection |

TABLE 1-continued

Sample info

| Sample ID | Source | Sample ID | Source | Sex | Rejection | Note |
|---|---|---|---|---|---|---|
| E8 | urine microvesicles | C8 | urine cells | M | No | No rejection, Acute tubular injury |
| E9 | urine microvesicles | C9 | urine cells | M | Yes | Antibody mediated rejection acute |
| E10 | urine microvesicles | C10 | urine cells | F | Yes | Acute cellular rejection, mild/AIN |
| E11 | urine microvesicles | C11 | urine cells | F | No | No rejection, Acute tubular injury |
| E12 | urine microvesicles | C12 | urine cells | F | Yes | Acute cellular rejection, IA |
| E13 | urine microvesicles | C13 | urine cells | M | No | No rejection |
| E14 | urine microvesicles | C14 | urine cells | M | Yes | Acute cellular rejection, mild, plasma rich |
| E15 | urine microvesicles | C15 | urine cells | M | Yes | Acute cellular rejection mild + Antibody mediated rejection |
| E16 | urine microvesicles | C16 | urine cells | M | Yes | Cellular rejection |
| E17 | urine microvesicles | C17 | urine cells | F | No | No rejection, Acute tubular injury |
| E18 | urine microvesicles | C18 | urine cells | M | Yes | Antibody mediated rejection mild |
| E19 | urine microvesicles | C19 | urine cells | F | No | No rejection, Acute tubular injury |
| E20 | urine microvesicles | C20 | urine cells | M | No | No rejection, Acute tubular injury |
| E21 | urine microvesicles | C21 | urine cells | M | No | No rejection, Acute tubular injury |
| E22 | urine microvesicles | C22 | urine cells | M | Yes | Acute cellular rejection, IA |
| E23 | urine microvesicles | C23 | urine cells | F | Yes | Antibody mediated rejection chronic |
| E24 | urine microvesicles | C24 | urine cells | M | Yes | Acute cellular rejection, IB |
| E25 | urine microvesicles | C25 | urine cells | M | No | No rejection |
| E26 | urine microvesicles | C26 | urine cells | M | No | No rejection, Acute tubular injury |
| E27 | urine microvesicles | C27 | urine cells | M | Yes | Antibody mediated rejection chronic |
| E28 | urine microvesicles | C28 | urine cells | F | No | No rejection, Acute tubular injury |

The OpenArray® (OA) Human Inflammation Panel was tested. In total, 586 target assays were run, with 21 endogenous control assays.

Briefly, the study design was as follows: 20 ml urine sample was centrifuged 2000×g for 20 minutes. The supernatant was then processed to extract microvesicle RNA using the urine clinical sample concentrator (uCSC), as described, e.g., in PCT Application Publication Nos. WO 2014/107571, WO 2015/021158, WO 2016/007755, and WO 2016/054252, the contents of each of which are hereby incorporated by reference in their entirety. The pellet was then processed to extract cellular RNA using the Promega ReliaPrep kit according to the manufacturer's instructions. RNA was eluted in 16 μl nuclease-free $H_2O$. 14 μl used in RT using VILO cDNA synthesis kit according to the manufacturer's instructions. 10 μl used in pre-amplification with 12 cycles pre-amplification. Pre-amplification reactions were diluted 1:10 in 1×TE buffer and mixed 1:1 with OA real-time PCR master mix prior to loading onto OpenArray® plate.

RNA profiling was performed as follows: The OpenArray® Human Inflammation Panel was run through TaqMan® qPCR assays, which included 586 target assays of genes that have been studied as targets for a range of inflammatory diseases. The following 21 endogenous control assays were also run: G6PD, POLR2A, IPO8, CASC3, YWHAZ, CDKN1A, UBE2D2, HMBS, UBC, HPRT1, 18S, RPLP0, ACTB, PPIA, GAPDH, PGK1, B2M, GUSB, HPRT1, TBP, and TFRC.

Figure 2:
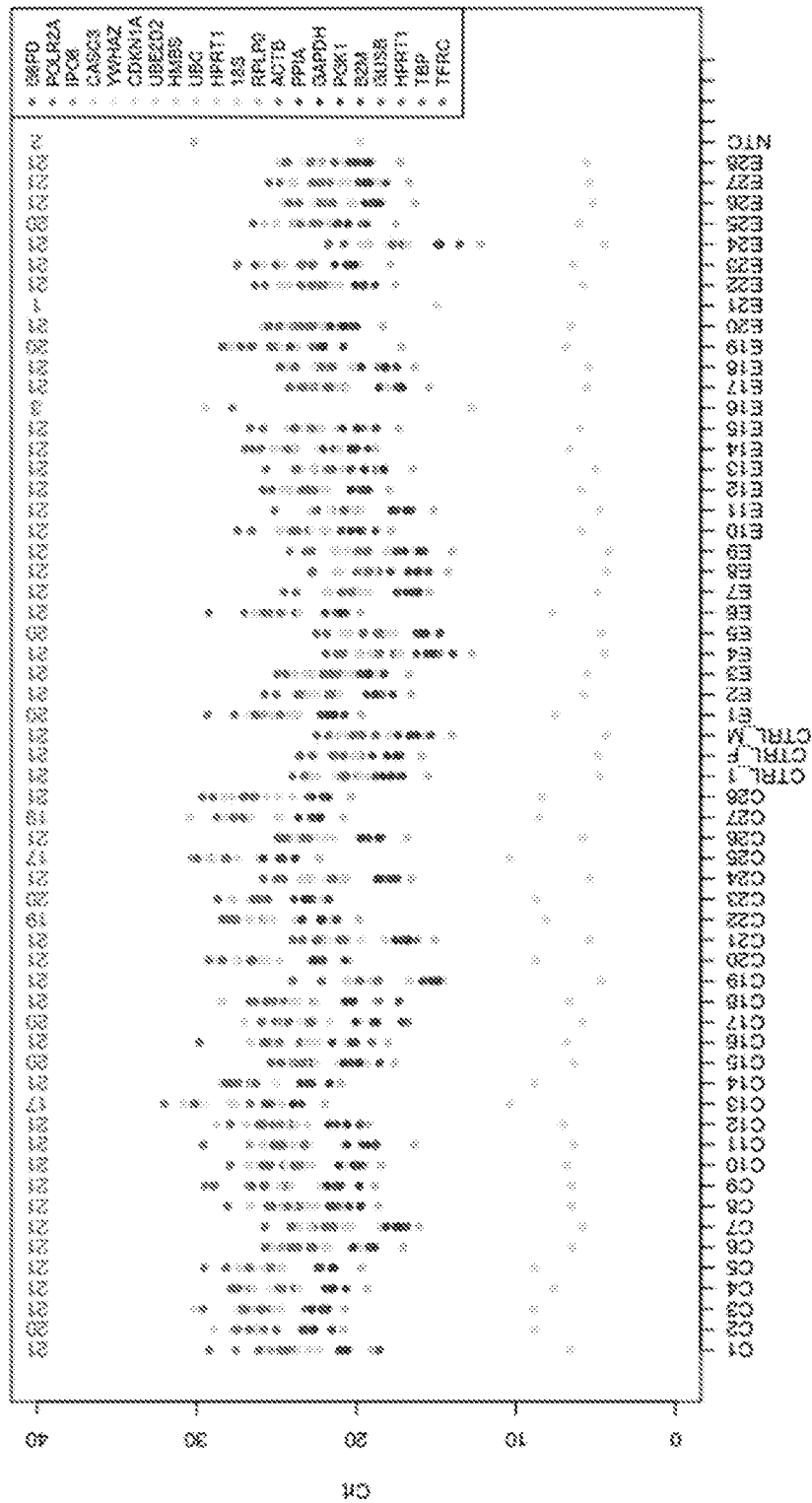
FIG. 2 is a graph depicting the raw data for 21 endogenous control assays. The 21 controls are shown in the legend in the figure.

The raw data from 607 assays for each sample is shown in FIG. 1, and the raw data from the 21 endogenous control assays is shown in FIG. 2. The numbers at the top of each of FIG. 1 and FIG. 2 represent the total number of assays that had a measurable readout. The width in each violin plot reflects the number of data points. Samples C1-C28 represent the cell pellet samples, CTRL represent the three controls, and samples E1-E28 represent the microvesicle samples. NTC represents the no template control.

Figure 3A:
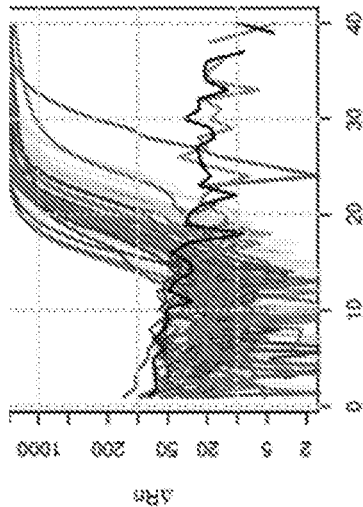
FIGS. 3A, 3B, 3C, 3D, 3E, 3F, and 3G are a series of graphs depicting normalization of the assay results using the following criteria: (i) excluding assays with minimum Crt>29; (ii) endogenous control assays; and (iii) 15≤mean Crt≤22. Normalization resulted in these seven control assays using conservative selection: UBC (FIG. 3A), RPLP0 (FIG. 3B), ACTB (FIG. 3C), PPIA (FIG. 3D), GAPDH (FIG. 3E), PGK1 (FIG. 3F), and B2M (FIG. 3G). Each curve in FIGS. 3A-3G represents a sample, and the black line represents no template control (NTC).
Figure 3B:
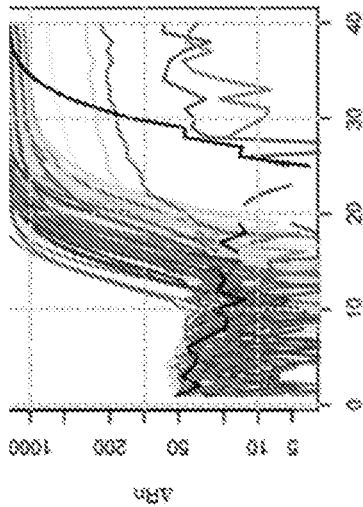
Figure 3C:
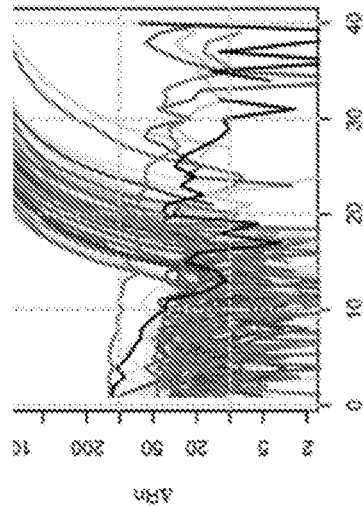
Figure 3D:
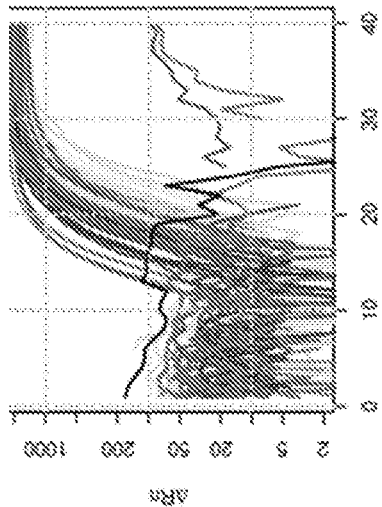
Figure 3E:
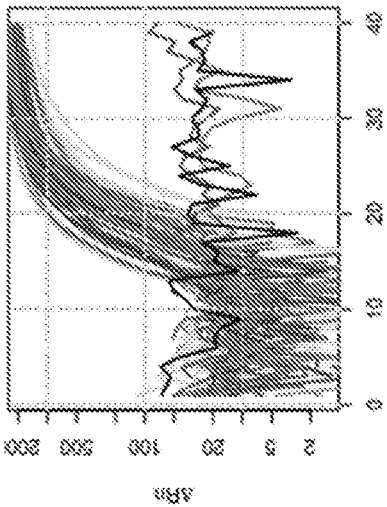
Figure 3F:
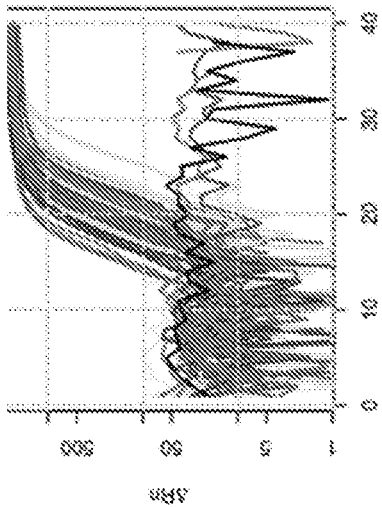
Figure 3G:
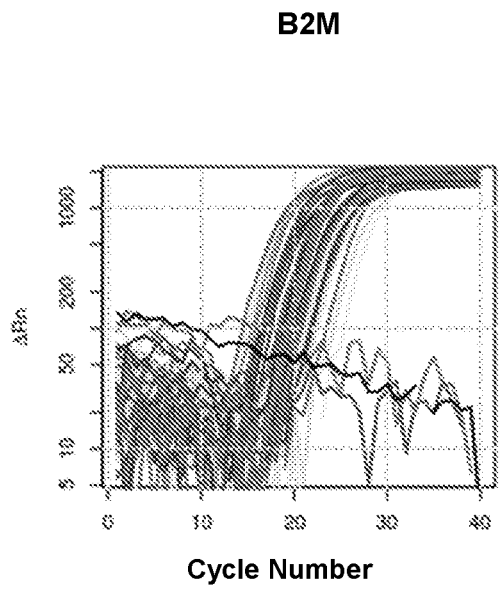

FIGS. 3A-3G are a series of curves for the normalized assay results. Normalization was performed using the following criteria: (i) excluding assays with minimum Crt>29; (ii) endogenous control assays; and (iii) 15≤mean Crt≤22. Normalization resulted in these seven control assays using conservative selection: UBC (FIG. 3A), RPLP0 (FIG. 3B), ACTB (FIG. 3C), PPIA (FIG. 3D), GAPDH (FIG. 3E), PGK1 (FIG. 3F), and B2M (FIG. 3G).

Figure 4A:
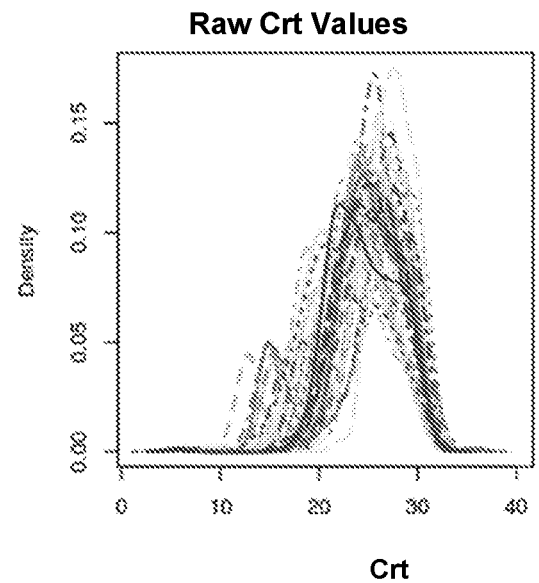
FIGS. 4A and 4B are a series of graphs depicting the normalization results for the raw Crt values (FIG. 4A) and the deltaCt (ΔCt) control normalized values (FIG. 4B). In these studies, normalization was calculated by subtracting the mean Crt value for the 7 control assays from FIGS. 3A-3G from the raw Crt values. Each curve in FIGS. 4A and 4B represents a sample, and the NTC, E16, and E21 were excluded from the results.
Figure 4B:
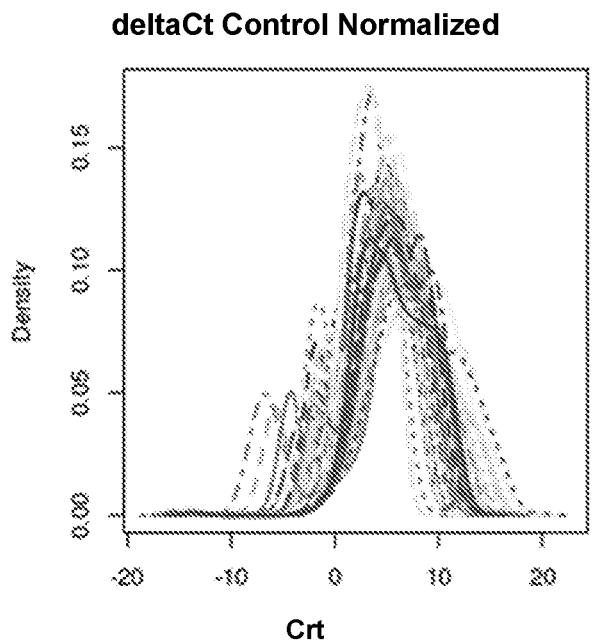

FIGS. 4A and 4B present the normalization results for the raw Crt values (FIG. 4A) and the deltaCt (ΔCt) control normalized values (FIG. 4B). Normalization was calculated by subtracting the mean Crt value for the 7 control assays from FIGS. 3A-3G from the raw Crt values.

Figure 5:
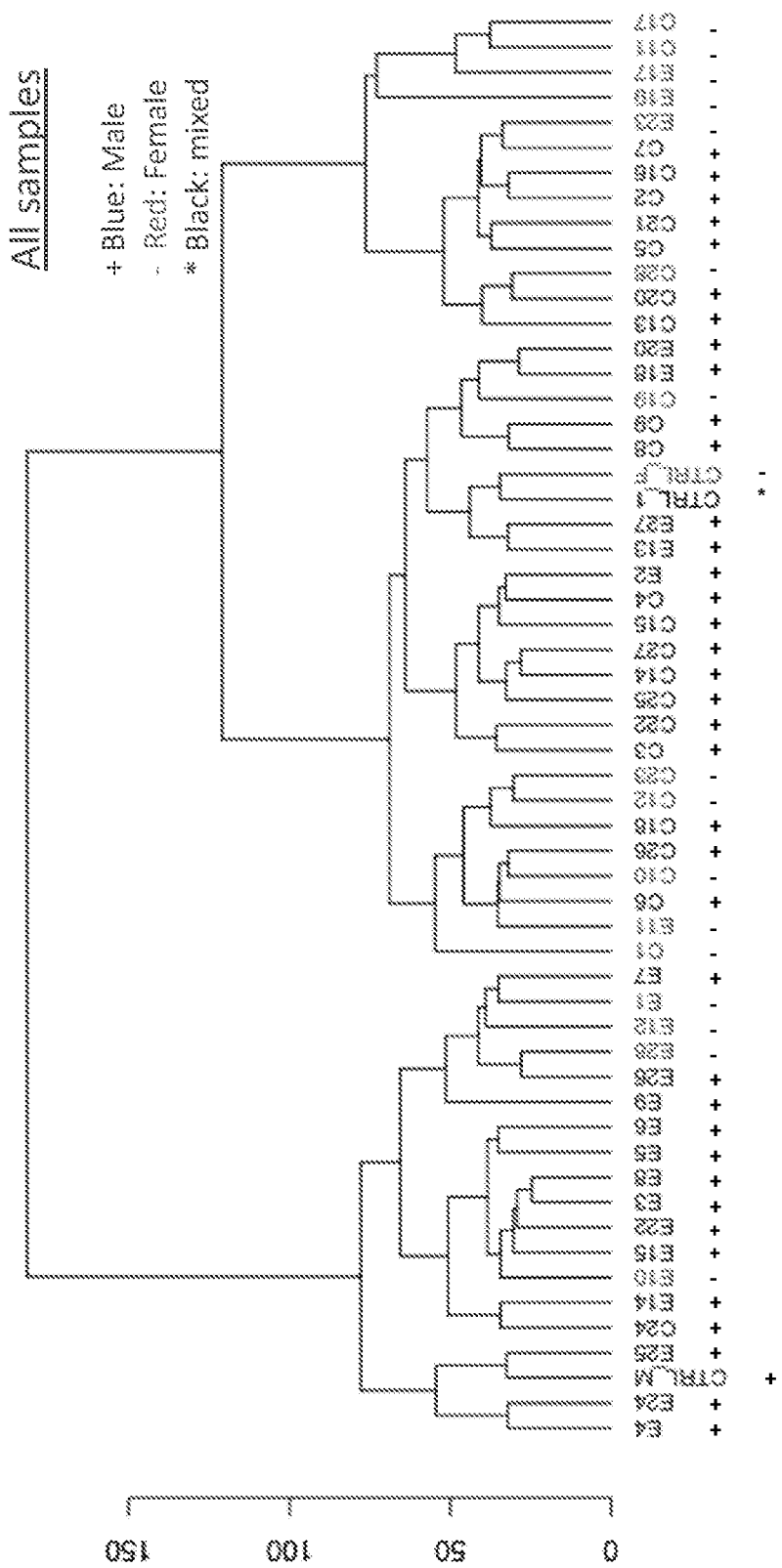
FIGS. 5 and 6 are a series of graphs depicting the overall clustering for the samples that were assayed.
Figure 6:
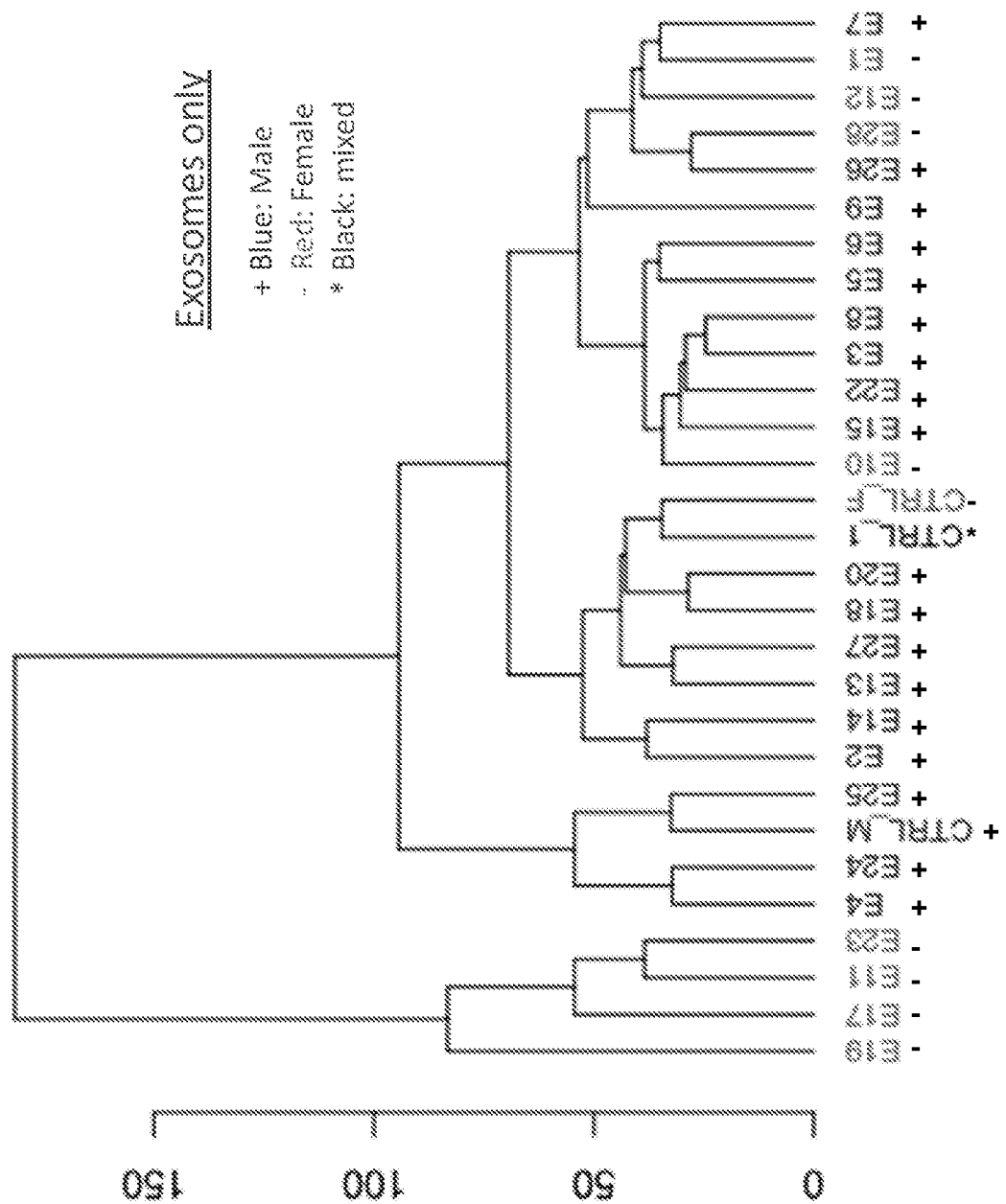

FIGS. 5 and 6 are a series of graphs depicting the overall clustering for the samples that were assayed. FIG. 5 depicts all samples, while FIG. 6 depicts the microvesicle only sample. These graphs depict good separation of cell pellet samples (C samples) and microvesicle samples (E samples), including male-specific samples. It should be noted that there were more male samples assayed.

Figure 7A:
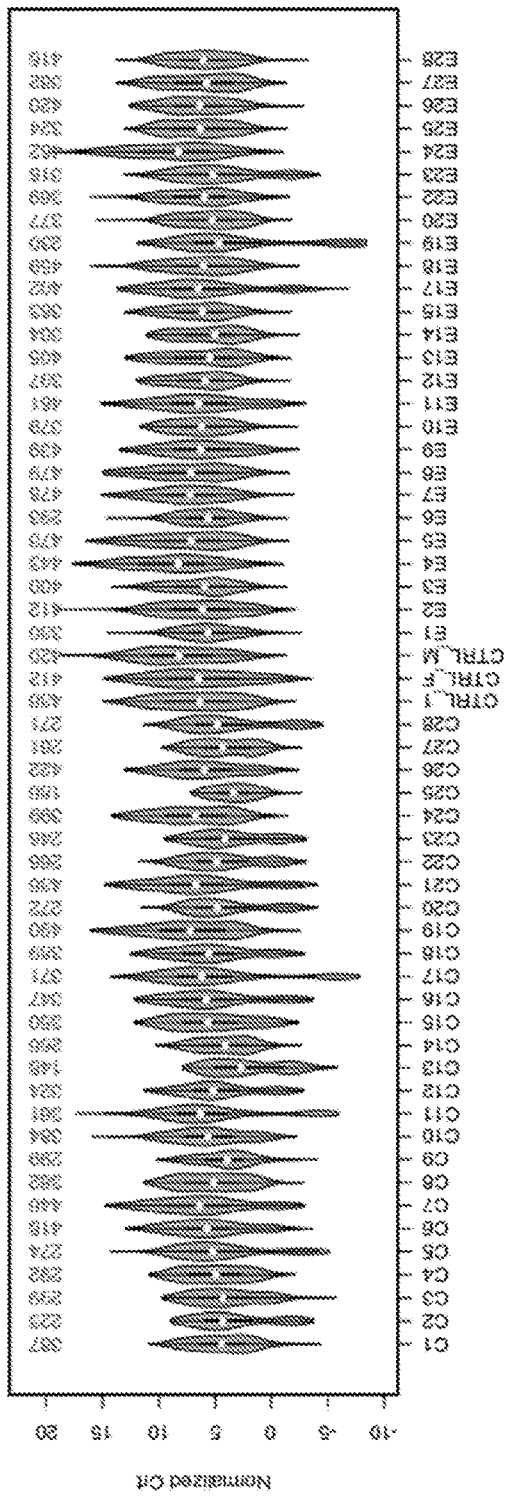
FIGS. 7A and 7B are a series of graphs comparing the results of 549 target assays (FIG. 7A) and 549 target assays with missing value imputation (FIG. 7B). Imputation was calculated using a probabilistic PCA model, where assays that were undetermined in >80% of samples.
Figure 7B:
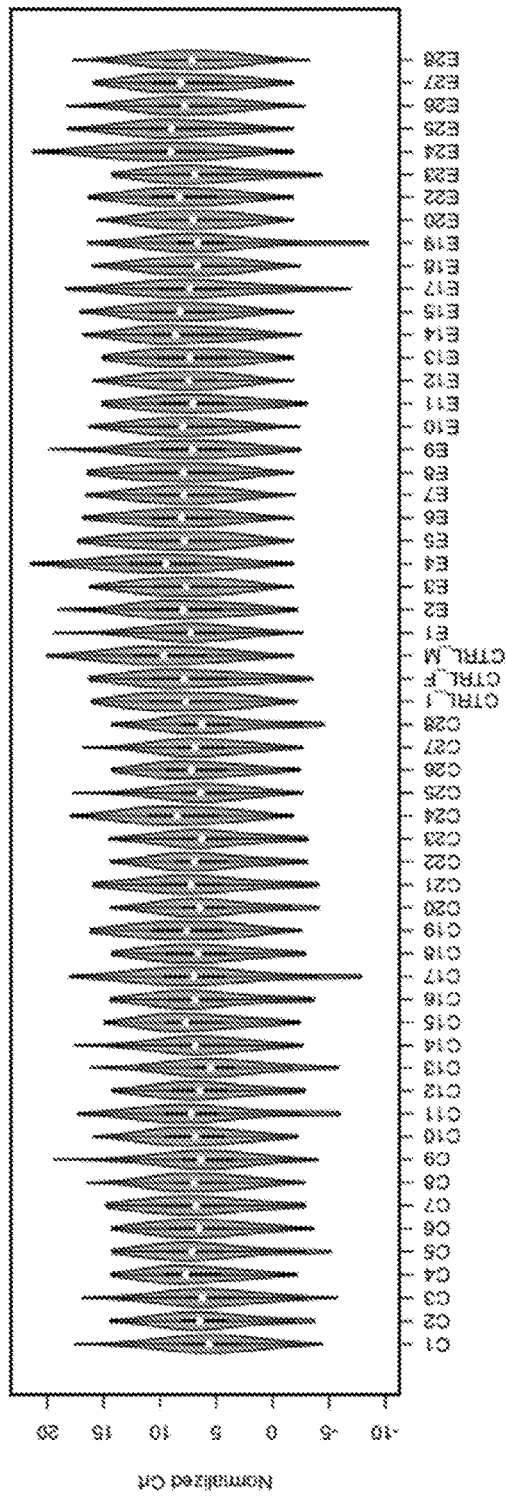

FIGS. 7A and 7B are a series of graphs comparing the results of 549 target assays (FIG. 7A) and 549 target assays with missing value imputation (FIG. 7B). Imputation was calculated using a probabilistic PCA model, where assays that were undetermined in >80% of samples.

Figure 8:
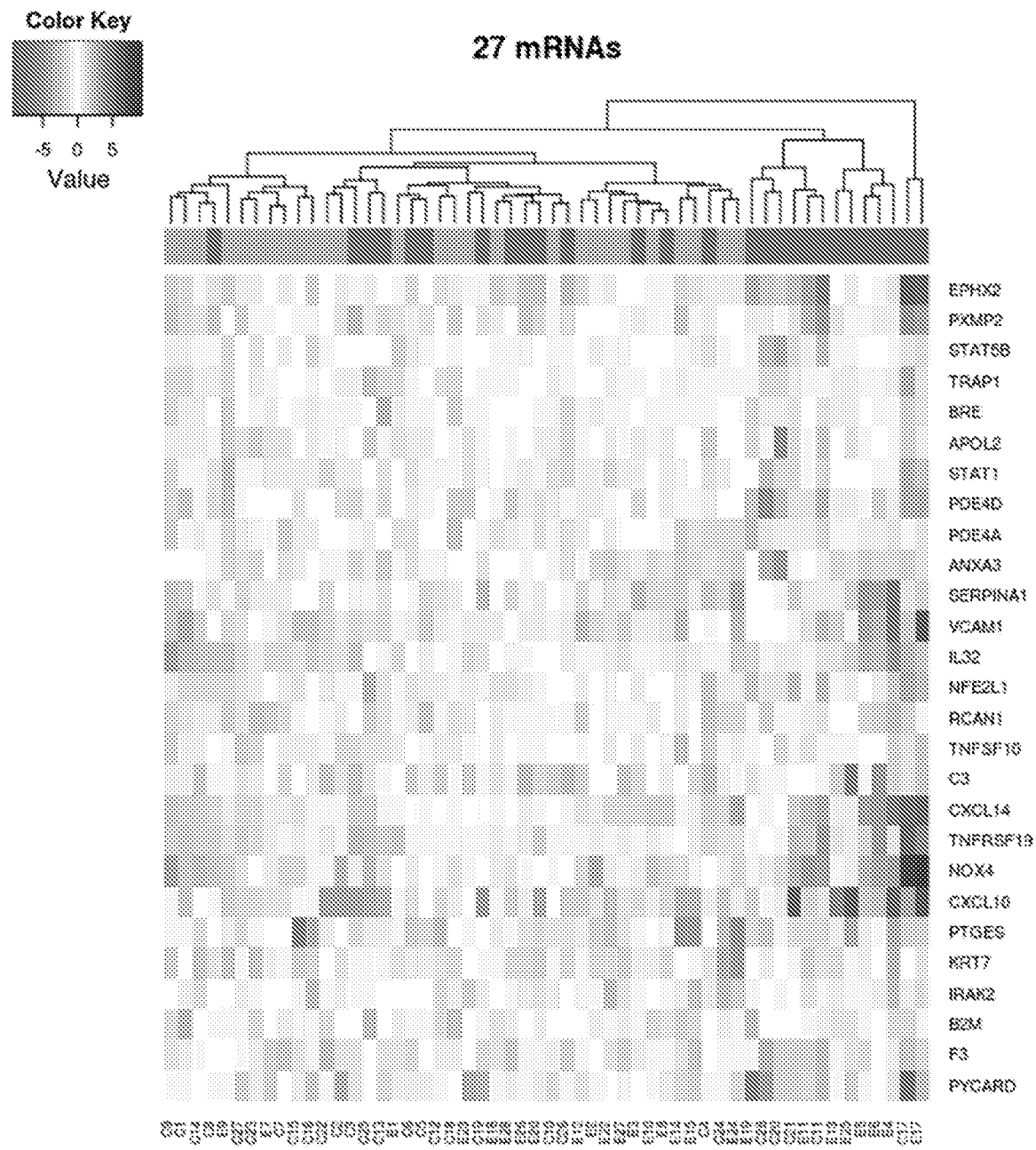
FIGS. 8, 9 and 10 are a series of plots depicting mRNA analysis from all samples in rejection vs. non-rejection subjects. The plots were generated using a two-group contrast, t-test based method, where significant mRNAs had a p-value <0.05. Each row in each plot is median-centered, with the warmer tones representing higher abundance values, and the cooler tones representing lower abundance values. In the color bar on the top of each plot, the darker green color represents no rejection samples, and the lighter orange color represents rejection samples.
Figure 9:
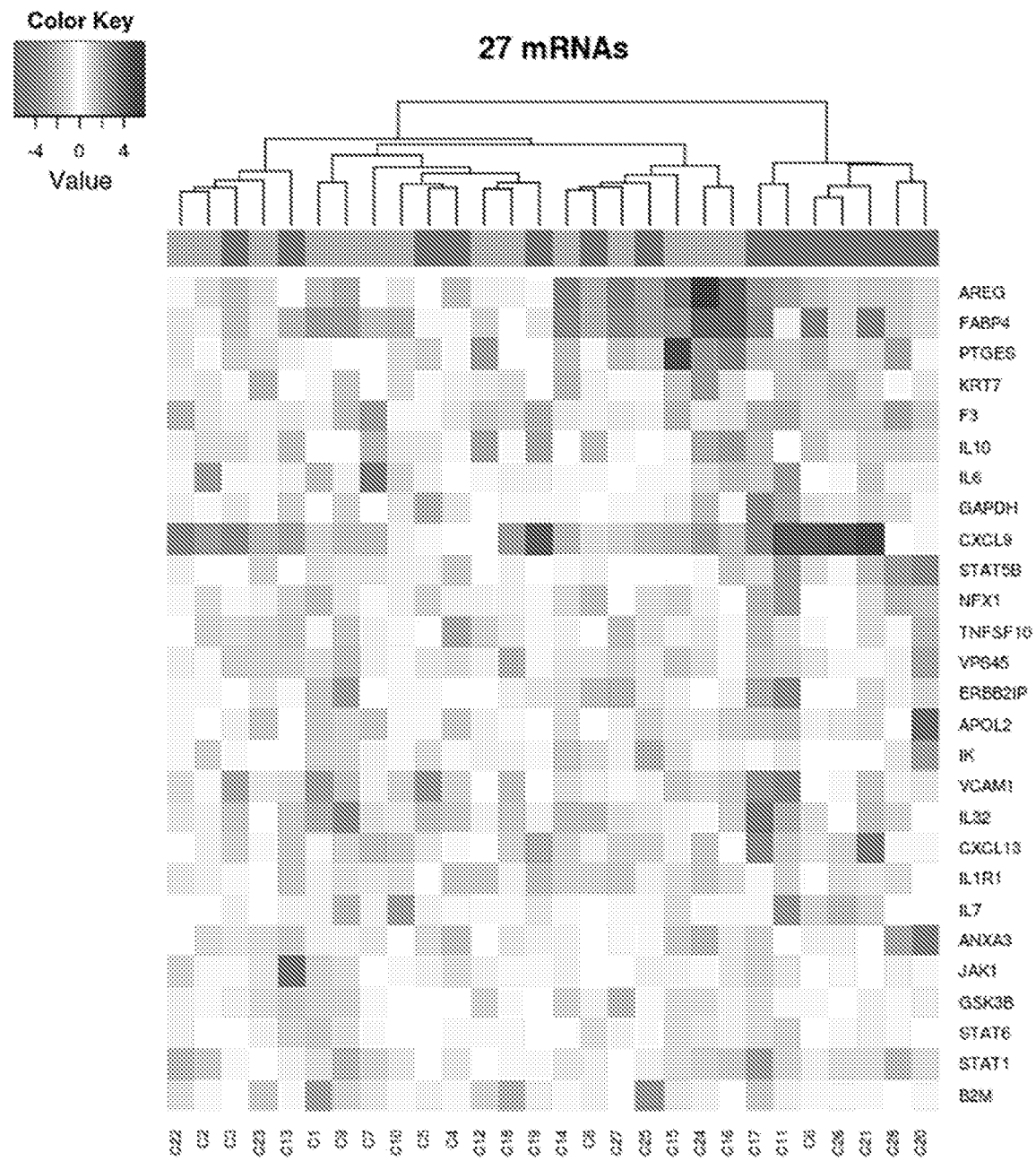
Figure 10:
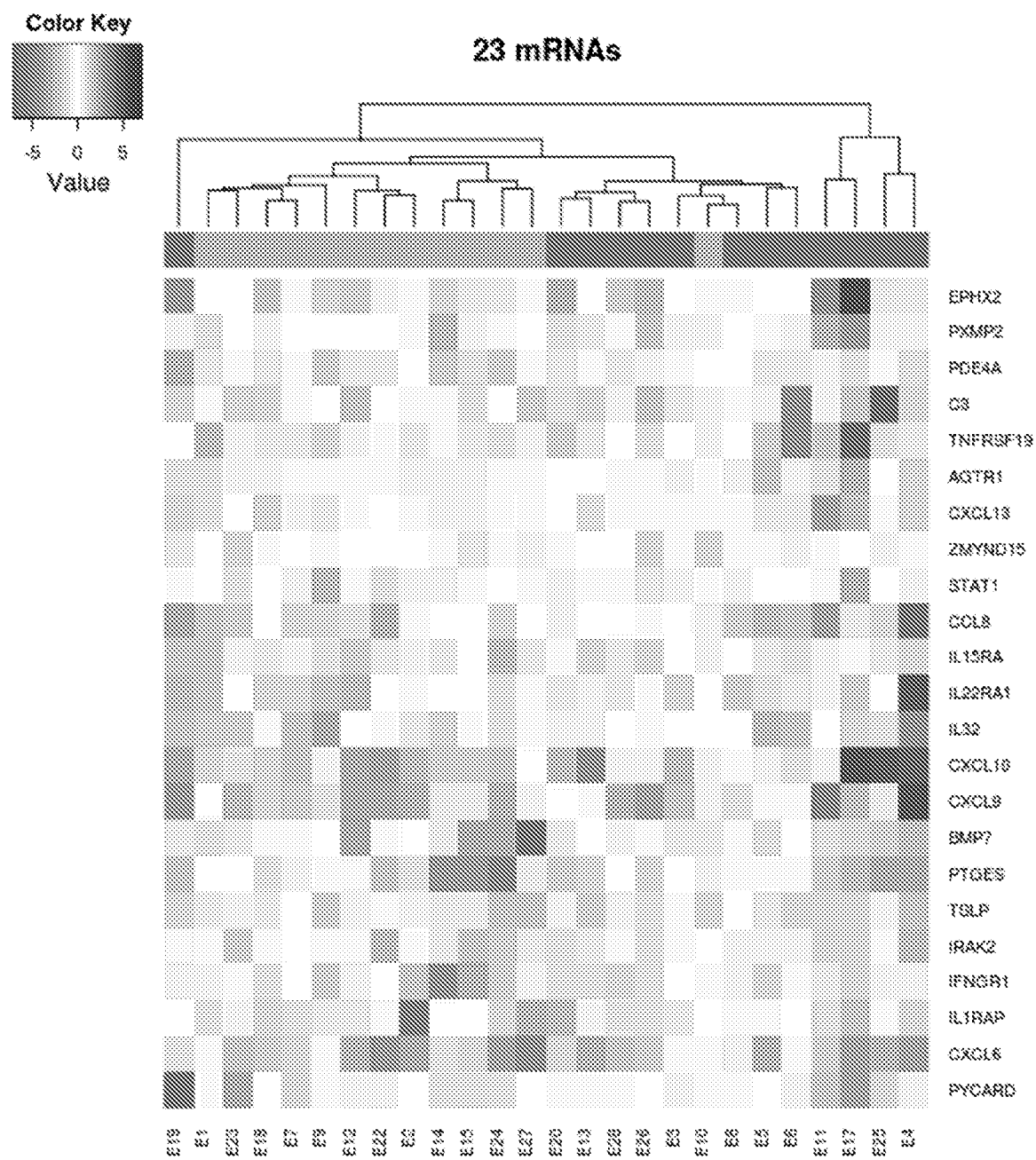

FIGS. 8, 9 and 10 are a series of plots depicting mRNA analysis from all samples in rejection vs. non-rejection subjects. The plots were generated using a two-group contrast, t-test based method, where significant mRNAs had a p-value <0.05. Each row in each plot is median-centered, with the warmer tones representing higher abundance values, and the cooler tones representing lower abundance values. In the color bar on the top of each plot, the darker green color represents no rejection samples, and the lighter orange color represents rejection samples. FIG. 8 is the plot for all samples tested, FIG. 9 is the plot for only the cell pellet samples, and FIG. 10 is the plot for only the microvesicle samples. The two outliers shown in FIG. 10 have been accounted for: in E10, the subject had allergic interstitial nephritis (AIN), which can lead to an ambiguous diagnosis; and in E19, the sample was of a low quality.

Thus, a gene signature derived from microvesicles in a urine sample performed the best in differentiating patients who experienced kidney transplant rejection from those patients who did not exhibit a symptom or other indication of transplant rejection.

Example 2: Discovery and Validation of a Urinary Exosomes mRNA Signature for the Diagnosis of Human Kidney Transplant Rejection Patients with end stage renal disease usually undergo transplantation, however, as many as 10-15% of these patients develop acute kidney rejection. Methods for monitoring clinical rejection include increase in serum creatinine and urinary protein secretion. These methods are not very accurate and may not reflect subclinical rejection. Currently, the patients are often monitored by repeat biopsies that may result in increased complications and cost. An accurate, non-invasive method would allow for earlier diagnosis and minimize the amount of immunosuppression needed to manage these patients. Extracellular vesicles such as exosomes (also referred to herein as microvesicles or the microvesicle fraction) are a promising new platform for biomarkers and can be used to monitor RNA and protein expression. Exosomes shed from the rejected kidney into the urine are likely originating from glomerular podocytes, renal tubular cells and from immune cells activated during rejection.

Figure 11:
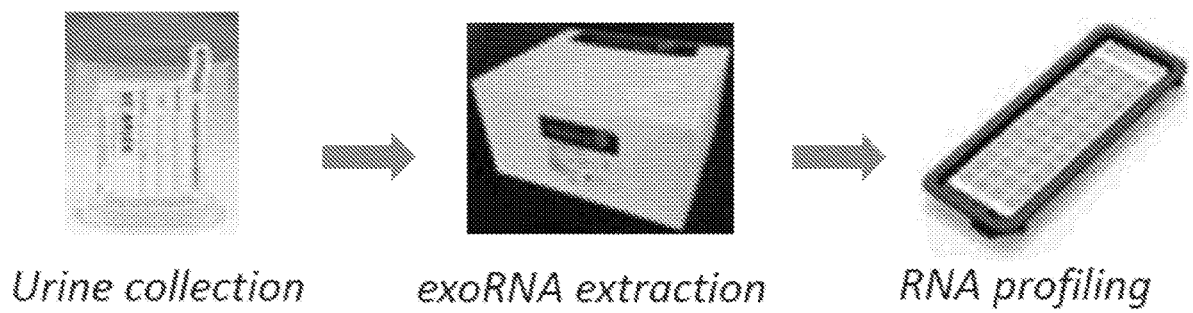
FIG. 11 is a schematic representation of the workflow of urine exoRNA isolation and expression profiling used in the studies presented in Example 2.

In the studies presented herein, urine samples were collected from patients undergoing a transplant kidney biopsy for clinical indications. A total of 66 urine samples across two cohorts (38 rejections, 28 non-rejections) were collected. RNA from both the urinary cell pellets and exosomes were isolated from up to 20 mls urine for expression profiling. Two patient cohorts were screened, first to generate a candidate marker panel (training) and a second to verify the performance of the smaller panel (test). RNA from the exosomes, also referred to herein as ExoRNA, was reverse transcribed and pre-amplified prior to analysis of RNA signature using the OpenArray® Human Inflammation Panel. OpenArray® is a TaqMan qPCR array. Human Inflammation Panel consists of 586 target and 21 endogenous control assays. An overview of the work flow of urine exoRNA isolation and expression profiling is shown in FIG. 11. An overview of the rejection criteria for the urine samples from kidney patients in a training cohort is shown below in Table 2.

TABLE 2

| Urine samples from kidney transplant patients (training cohort) | |
|---|---|
| Rejection Criteria | Number of Samples |
| Cellular rejection including borderline rejection | 7 |
| Antibody mediated rejection (AMR): acute or chronic active | 7 |
| No rejection | 14 |
| Total | 28 |

Figure 12A:
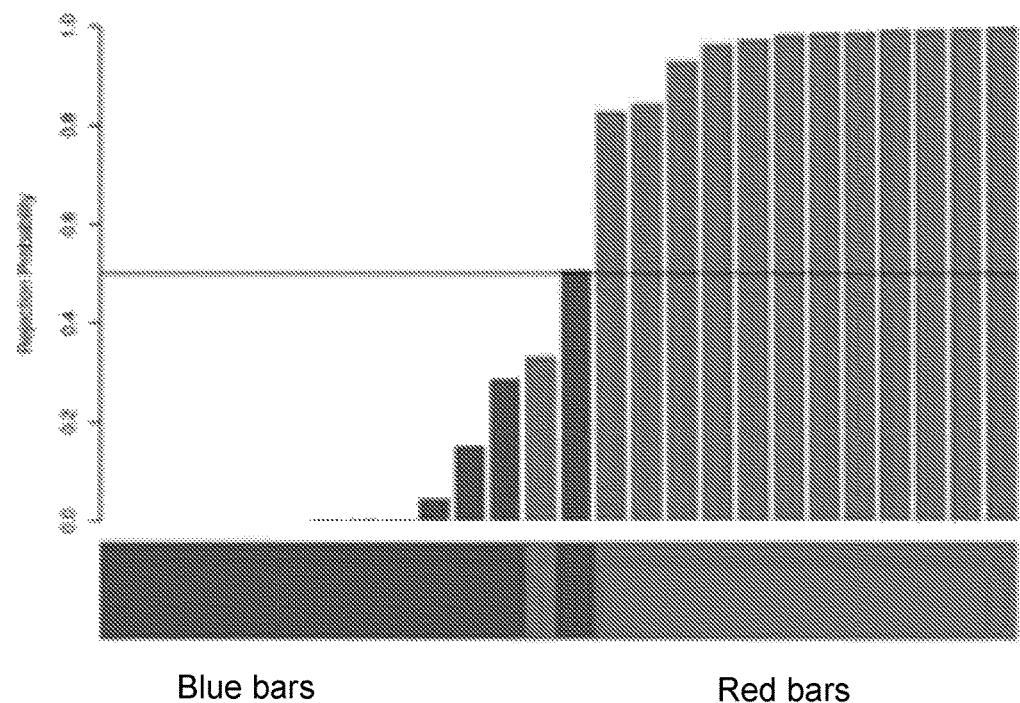
Figure 12B:
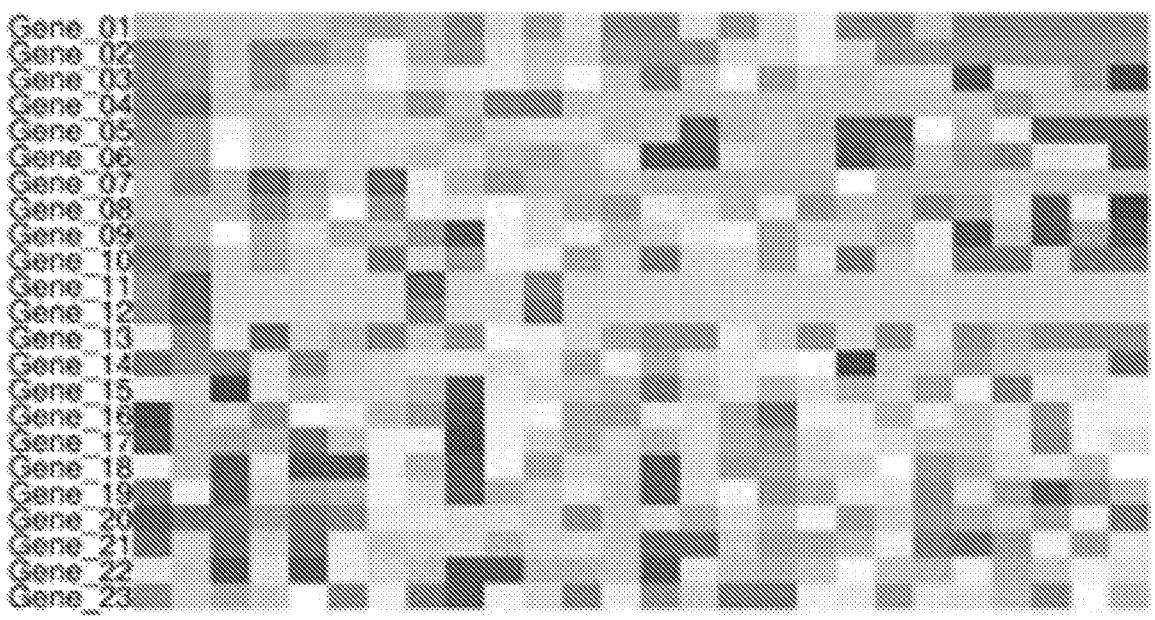

The expression of 207 (34%) to 518 (85%) genes was detected. Two samples were excluded from analysis due to low RNA yield. Analysis of mRNA expression in urinary pellets and exosomes, from the training cohort samples, identified genes that were differentially regulated. The exosome samples identified 23 significantly differentially expressed genes (FIGS. 12A-12C). The 23 genes are shown in FIG. 12C. The genes identified from exosomal RNA performed significantly better in correctly differentiating between rejection and non-rejection compared to the cell pellet RNA.

In a second, test cohort (referred to herein as test cohort), the extracted samples were again run on the OpenArray® Human Inflammation Panel. One sample was excluded due to low RNA yield.

An overview of the rejection criteria for the urine samples from kidney patients in a training cohort is shown below in Table 3.

TABLE 3

| Urine samples from kidney transplant patients (test cohort) | |
|---|---|
| Rejection Criteria | Number of Samples |
| Cellular rejection including borderline rejection | 14 |
| Antibody mediated rejection (AMR): acute or chronic active | 4 |
| Cellular and AMR | 6 |
| No rejection | 14 |
| Total | 38 |

Figure 13A:
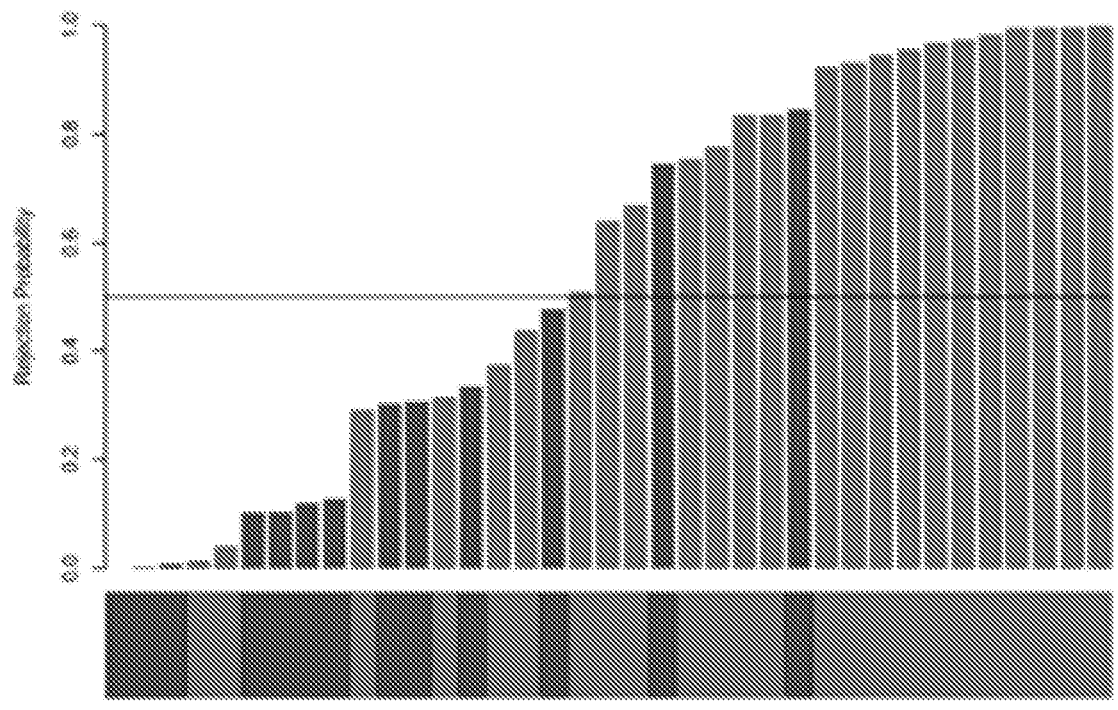
Figure 13B:
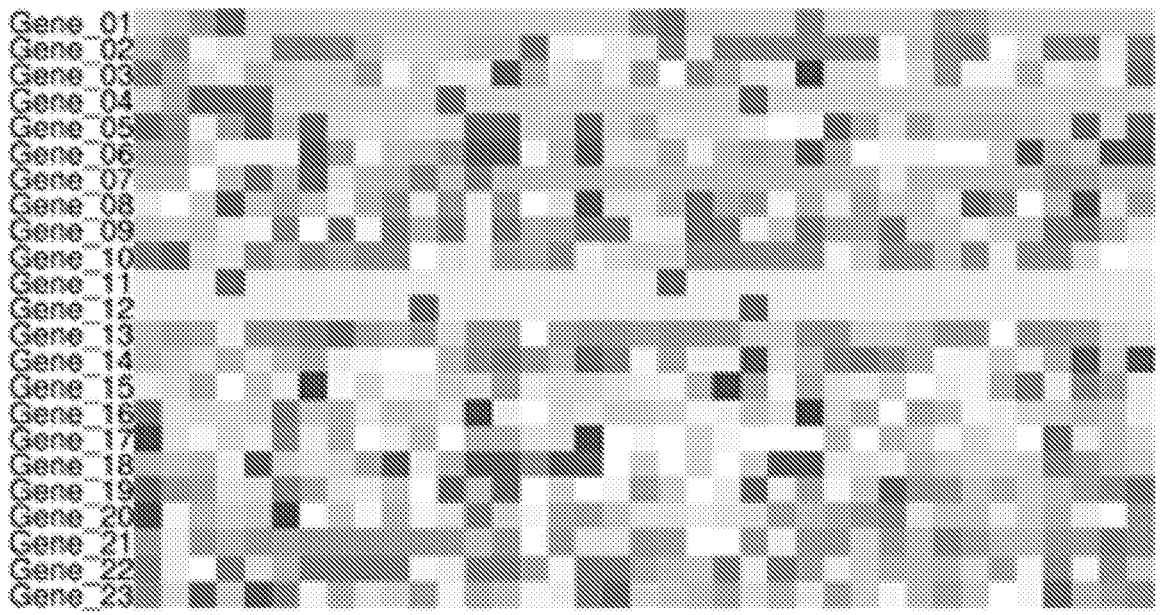
Figure 14:
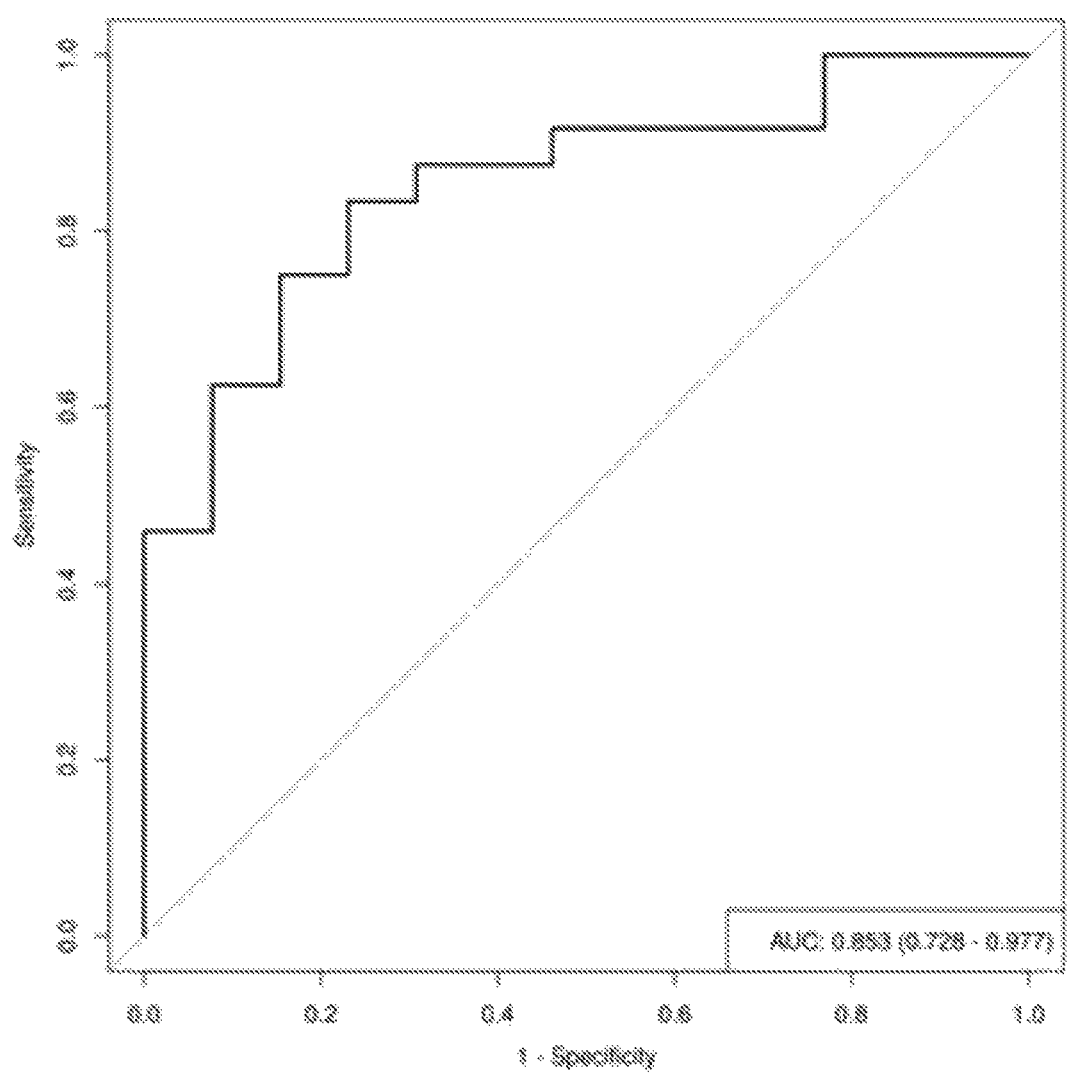
FIG. 14 is a graph depicting ROC curve analysis of the 23-gene signature in test cohort.

The performance of the 23-gene signature was evaluated (FIGS. 13A-13C). The 23 genes are shown in FIG. 13C. ROC analysis of the signature demonstrated an AUC of 0.853 (FIG. 14).

Thus, the studies presented herein have identified a 23-gene signature in urine exosomes that is useful in characterizing patients with kidney rejection. Analysis of cellular RNA from urine was unable to generate such a signature.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:

1. A method of treating kidney transplant rejection in a human subject in need thereof, the method comprising administering to a human subject identified as having a kidney rejection at least one kidney transplant rejection therapy, wherein the human subject is identified as having a kidney transplant by comparing the level of expression of a panel of biomarkers comprising CXCL9, IFNGR1, CXCL10, PXMP2, TNFRSF19, IL32, AGTR1, EPHX2, PDE4A, IRAK2, IL22RA1, IL1RAP, CXCL13, CXCL6, PTGES, STAT1, TSLP, BMP7, IL15RA, CCL8, PYCARD, C3, ZMYND15 in nucleic acids extracted from a microvesicle fraction isolated from a urine sample from the human subject with a control level of expression of the panel of biomarkers to identify kidney transplant rejection in the human subject, wherein the control level of expression of the panel of biomarkers is from a human patient who is experiencing kidney transplant rejection, and the level of expression of the panel of biomarkers in the human subject is similar to the control level of expression of the panel of biomarkers, and the human subject is identified as having a kidney transplant rejection, or wherein the control level of expression of the panel of biomarkers is from a human patient who has not experienced any symptom of kidney transplant rejection, and the level of expression of the panel of biomarkers from the human subject is different than the control level of expression of the panel of biomarkers and the human subject is identified as having a kidney transplant rejection.

2. The method of claim 1, wherein the nucleic acids are extracted using a method comprising (i) processing microvesicles to exclude proteins, lipids, debris from dead cells, and other contaminants; (ii) purifying microvesicles using ultracentrifugation or a nanomembrane ultrafiltration concentrator; and (iii) washing the microvesicles.

* * * * *